(12) United States Patent
Africk et al.

(10) Patent No.: US 7,543,480 B2
(45) Date of Patent: Jun. 9, 2009

(54) SYSTEM AND METHOD FOR ULTRASONIC MEASURING OF PARTICLE PROPERTIES

(75) Inventors: Steven A. Africk, Waban, MA (US); Clark K. Colton, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 331 days.

(21) Appl. No.: 11/272,032

(22) Filed: Nov. 14, 2005

(65) Prior Publication Data
US 2006/0178581 A1 Aug. 10, 2006

Related U.S. Application Data

(60) Provisional application No. 60/627,927, filed on Nov. 15, 2004.

(51) Int. Cl.
*G01N 11/10* (2006.01)
(52) U.S. Cl. .............. 73/54.25; 600/440; 73/53.01; 73/54.24; 73/61.66; 73/61.71
(58) Field of Classification Search .............. 73/54.25; 600/440; 702/19
See application file for complete search history.

(56) References Cited

U.S. PATENT DOCUMENTS

| | | | |
|---|---|---|---|
| 3,208,286 A | 9/1965 | RIchard | |
| 4,112,735 A | 9/1978 | McKnight | |
| 4,112,773 A | 9/1978 | Abts | |
| 4,208,915 A | 6/1980 | Edwards | |
| 4,237,720 A | 12/1980 | Abts | |
| 4,412,451 A | 11/1983 | Uusitalo et al. | |
| 4,478,072 A | 10/1984 | Brown | |
| 4,509,360 A | 4/1985 | Erwin et al. | |
| 4,527,420 A | 7/1985 | Foote et al. | |
| 4,718,269 A | 1/1988 | Der Kinderen | |
| 4,739,662 A | 4/1988 | Foote | |
| 4,988,190 A | 1/1991 | Miles | |
| 5,392,638 A | 2/1995 | Kawahara | |
| 5,487,387 A | 1/1996 | Trahey et al. | |
| 5,792,962 A | 8/1998 | Constant et al. | |
| 5,969,237 A * | 10/1999 | Jones et al. | 73/61.75 |
| 6,029,507 A | 2/2000 | Faber et al. | |
| 6,205,848 B1 | 3/2001 | Faber et al. | |
| 6,487,894 B1 | 12/2002 | Dukhin et al. | |
| 6,573,991 B1 | 6/2003 | Debreczeny et al. | |
| 6,604,408 B2 | 8/2003 | Dosramos et al. | |
| 6,748,815 B2 * | 6/2004 | Povey et al. | 73/865.5 |
| 6,796,195 B2 * | 9/2004 | Povey et al. | 73/865.5 |
| 6,945,096 B1 | 9/2005 | Jones et al. | |
| 7,360,403 B2 * | 4/2008 | Jones et al. | 73/61.75 |
| 2004/0045378 A1 | 3/2004 | Coghill | |
| 2004/0065160 A1* | 4/2004 | Povey et al. | 73/865.5 |

(Continued)

*Primary Examiner*—Samir M Shah
(74) *Attorney, Agent, or Firm*—Pearl Cohen Zedek Latzer, LLP; Mark Cohen

(57) ABSTRACT

Devices, systems and methods for measuring and detecting properties of a variety of particles or cells in suspension. Properties, such as, for example, velocity of particles, concentration and/or size may be measured according to the methods of the invention. Acoustic energy may be introduced to a focal zone and narrow band interrogating signals may be used. The acoustic energy may cause movement or streaming of the fluid or suspension. The acoustic streaming may allow a Doppler effect measurement without any other source of velocity.

24 Claims, 21 Drawing Sheets

U.S. PATENT DOCUMENTS

| | | |
|---|---|---|
| 2005/0114046 A1 | 5/2005 | Metcalf et al. |
| 2005/0150275 A1 | 7/2005 | Panetta et al. |
| 2006/0178581 A1* | 8/2006 | Africk et al. ................. 600/440 |
| 2008/0066551 A1* | 3/2008 | Panetta ........................ 73/584 |

* cited by examiner

200
SYSTEM AND METHOD FOR ULTRASONIC MEASURING OF PARTICLE PROPERTIES

CROSS REFERENCE TO RELATED APPLICATIONS

This Application claims the benefit of the U.S. Provisional Application U.S. Ser. No. 60/627,927, filed on Nov. 15, 2004 which is fully incorporated herein.

FIELD OF THE INVENTION

The present invention relates to measuring and detecting of properties of particles for example in suspension, for example by using ultrasonic techniques.

BACKGROUND OF THE INVENTION

Ultrasonic methods and systems may be used to measure the concentration and other properties of suspended particles or other materials, including, for example, biologic materials. For example, there is a need to measure concentration of human islets in preparations for human transplantation. These measurements can be combined with separate measures of the viability of the islets to determine the number of viable and dead cells in a preparation. There is also a need for systems that can measure properties of small particles on a nanoscale.

SUMMARY OF THE INVENTION

Embodiments of the present invention may include, for example, devices, systems and methods for measuring and detecting properties of a variety of particles or other materials, such as cells, in suspension. For example, to measure velocity of the particles/cells, their concentration and/or size by using an ultrasonic system based on the Doppler effect.

In some embodiments, narrow-band acoustic (e.g. ultrasonic) interrogating energy may be introduced to a focal zone within a sample containing particles to be tested to generate high levels of acoustic energy in a small volume and in a narrow frequency range. This may produce high levels of backscatter from this volume. The suspensions of particles may include particles in motion due to stirring or bulk flows as in a manufacturing process. The high levels of interrogating signals in the focal volume may induce velocities due to acoustic (Eckart) streaming. Particle velocities due to any of these sources may allow measurement of acoustic backscatter at frequencies differing from that of the interrogating energy by the Doppler effect. Backscattered time-domain signals may be converted by a Fast Fourier Transform ("FFT") algorithm to a high-resolution, narrow-band power spectrum, the shape of which provides the information about the particle suspension.

Embodiments of the invention may include processing of the receiving signal and determining properties such as velocities and size and concentration of particles from a high precision power spectrum of the signal. In addition some embodiments of the invention may include back wall reflection calibration, for example a system self-check.

BRIEF DESCRIPTION OF THE DRAWINGS

Embodiments of the invention may be understood and appreciated more fully from the following detailed description taken in conjunction with the drawing in which.

DETAILED DESCRIPTION OF THE INVENTION

Figure 1:
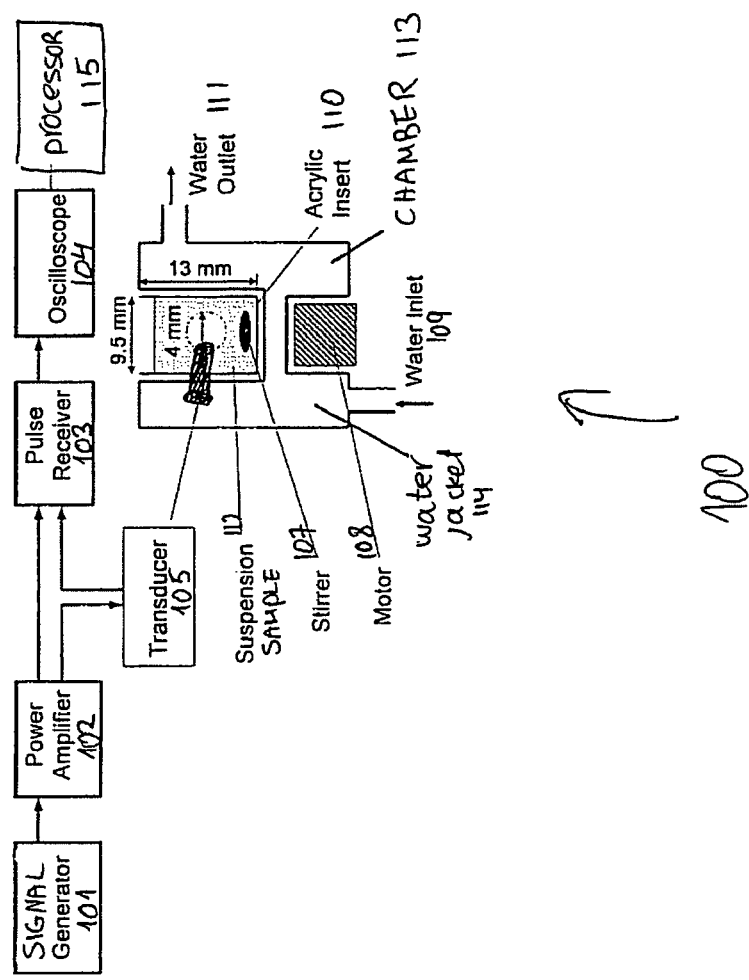
FIG. 1 is a schematic diagram of a system for measuring backscattered power in accordance with an embodiment of the invention.

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention. Various examples are given throughout this description. These are merely descriptions of specific embodiments of the invention. The scope of the invention is not limited to the examples given.

Unless specifically stated otherwise, as apparent from the following discussions, it is appreciated that throughout the specification, discussions utilizing terms such as "processing," "computing," "calculating," "determining," "deriving" or the like, refer to the action and/or processes of a processor, computer or computing system, or similar electronic or hardware computing device, that manipulates and/or transforms data represented as physical, such as electronic quantities within the computing system's registers and/or memories into other data similarly represented as physical quantities within the computing system's memories, registers or other such information storage, transmission or display devices.

The processes and displays presented herein are not inherently related to any particular computer, measurement device, electronic device or other apparatus. The desired structure for a variety of these systems will appear from the description below. In addition, embodiments of the present invention are not described with reference to any particular programming language, machine code, etc. It will be appreciated that a variety of programming languages, mathematical tools, electronic measurements tools, machine codes, etc. may be used to implement the teachings of the invention as described herein. Embodiments of the invention may be included on a medium or article such as a hard disc, CD, DVD, "disc on key", memory stick, or other memory unit having stored thereon instruction that when executed implement an embodiment of the invention, or having files or data corresponding to effects stored thereon.

Methods such as Ultrasonic Pulsed Doppler ("USPD") techniques may be based on the backscatter or reflection of ultrasonic acoustic energy from moving scattering objects that have an acoustic impedance contrast with the medium in which they are suspended. This acoustic contrast may be due, for example, to a difference in the density or the compressibility of the particles from that of the fluid, or both. These differences may give rise to a difference between the acoustic impedances—the product of the particle or fluid density and sound wavespeed, which product is proportional to the square root of the product of the density and the compressibility.

One principle of the measurement may be that the amount of acoustical energy backscattered from a given volume of a suspension may increase with the concentration of particles or cells with an impedance contrast within that volume. Thus, the strength of a signal backscattered from a volume insonified by an ultrasonic beam may be proportional to the concentration of suspended material in that volume.

In the long wavelength limit where the wavelength of the acoustical energy being scattered may be greater than the size of a weakly scattering (nonresonant) particle, i.e., $\lambda \geqq 2\pi a$ where $\lambda$ may represent the wavelength and "a" may represent the particle radius, the backscattered energy may be due to Rayleigh scattering and it may depend on the contrast between the compressibility and density of the particle and that of the fluid suspension medium, and the volume of the particle. For example, at the typical ultrasonic frequency of 15 MHz, the acoustic wavelength is 100 µm. For cells or other particles on the order of 10 µm or smaller the ratio $2\pi a/\lambda$ may be small ($\leqq 0.6$) and the backscatter has these properties. At higher frequencies and/or for larger particles, the backscattered power may become a function of other particle properties which may complicate interpretation of backscatter data.

Embodiments of the invention may also detect the velocity of motions of the fluid containing the backscattering particles. This motion may give rise to a shift in the frequency of the backscattered acoustic power due to the Doppler effect, wherein the fractional shift in the received frequency is twice the ratio of the velocity along the line of sight to the particle from the sound source and receiver to the velocity of sound in the fluid. For example, the ultrasonic energy at frequency $f_0$ incident on a scattering object may be related to the velocity v at which the object is moving away from a transducer. The backscattered ultrasonic energy received may have the frequency $f_0 - \Delta f$, where $\Delta f$ is given by the well-known formula: $\Delta f/f_0 = 2v/c$ where c is the velocity of sound in the fluid medium, approximately 1500 m/sec for water.

Embodiments of the invention may be used to measure, for example, the concentrations of a variety of particles of different sizes in suspension. Such embodiments may measure concentrations in the range from a few tenths of a percent to about 40% or more by volume of cells ($\geqq 10^6$/ml), cell aggregates (spheroids, $\geqq 300$/ml), Islets of Langerhans (human and murine, $\geqq 300$/ml), 200 nm diameter particles in an emulsion, and polymer beads with diameters as small as 40 nm, and nanoparticles on the order of 1-10 nm diameter. Measurement accuracy and precision on the order of 10% can be achieved.

Embodiments of the invention may for example allow concentration measurements of any particle species with acoustic contrast with a medium in which it is suspended. The measurement may be minimally invasive and it may be used without contact with the fluid being measured. Furthermore, backscatter spectra which may be generated by embodiments of the invention may provide information about the nature of the particles. For example, multiple spectra peaks may imply the existence of more than one type of particle and the velocities with which these particles move may provide information about them and the viscosity of the suspensions.

Particle movement or velocities may be generated in a suspension in a number of ways. For example, suspensions may be stirred or otherwise moved, creating a generally cylindrical pattern of motions. Downward motion may be created by the negative buoyancy of larger and more dense particles, which may tend to sink or precipitate out of solution. Fluid flows may also be generated by the interrogating ultrasound signal itself, which may be due to ultrasonic streaming or Eckart streaming, which is the generation of motion in open volumes of fluid by ultrasound, or simply "streaming." For example, if an ultrasonic beam with high intensity is incident on a liquid, the liquid may experience acceleration due to nonlinear effects and a macroscopic flow away from the transducer may develop. An advantage to using streaming may be the simplicity of not having to stir the suspension by other methods. In one embodiment of the present invention an advantage may be obtained such that particle velocities required to make the measurement arise due to ultrasonic streaming may be induced by the interrogating ultrasound itself.

Energy backscattered at frequencies other than the interrogating frequency may be easier to detect than that energy backscattered at the same frequency. This is because in a small chamber there may be reflections from walls which may be many orders of magnitude larger than backscatter from the particles. Separation, identification, and measurement of the small reflections from microscopic objects such as islets, cells, and submicron particles in the presence of the larger reflections at the same frequency may be difficult. In the parlance of detection theory, a very large dynamic range may be required in the presence of substantial measurement "clutter." However, when the backscattered energy is at a frequency that differs from that of the original interrogating signal the detection may be simpler because no other significant signals are present at the Doppler-shifted frequencies. Consequently, weak backscatter from low concentrations of scattering particles may be measured in the presence of other signals such as strong wall reflections or the original interrogating signal itself.

When using embodiments of the present invention, backscatter from a suspension of cells may occur in a band of Doppler-shifted frequencies, due in part to the distribution of particle velocities (or more precisely of the components of these velocities in the direction of the line between the scatterer and the transducer). The shape of the reflectivity spectrum (e.g. backscattered power vs. frequency) may contain additional information about the particles. For example, the maximum velocity that can be induced by a given level of stirring or acoustical streaming depends on the viscosity of a sample, which may depend on size distribution of the suspended scatterers. Likewise, under the influence of streaming alone, particles of different size may attain different velocities depending on possible particle interactions with the high acoustic fields or differing drag coefficients. In such cases, the reflection spectrum may include multiple peaks corresponding to the particle sizes.

FIG. 1 depicts a block diagram of a system according to one embodiment of the present invention. System 100 may include signal generator 101, power amplifier 102, pulse receiver 103 oscilloscope 104 and processor 1115. System 100 may also include tranducer 105, chamber 113 which may contain sample or suspension 112 and stirred 107. System 100 may analyze a sample or suspension 112 which may be of various sizes and volumes, and which may include particles suspended in a liquid.

System 100 may be used for measurements of reflected or backscattered power from, for example, sample 112 which may include cells, cell aggregates and polymer beads that may be negatively buoyant and may tend to sink the bottom of chamber 113 unless stirred. Other particles may be measured. System 100 may optionally include a magnetic or other stirrer bar 107 which may be used to keep the samples suspended and may also include a precision stirrer motor 108 which may be used to control stir rate. Magnetic stirrer bar 107 and/or precision stirrer motor 108 may not be used, for example, when neutrally buoyant particles, including most nanoparticles may be measured. The actual rotation rate of the stirrer bar may be measured with for example a precision stroboscope and may be kept, for example, to within 2% of 900 rpm. Any other suitable rotation rate or tolerance may be used. In some embodiments particles in the suspension may be set into motion by the action of a stirrer bar while in other embodiments the particles may be in motion due to bulk fluid flow. Other suitable stirring methods may be used.

System 100 may also include a water chamber 113 having a water jacket 114 with water inlet 109 and water outlet 111 for thermal cycling and temperature control. It may be marked to indicate the standard volume used for testing. A cover (not shown) may be placed loosely over the top of chamber 113 to prevent foreign objects from falling in. A level may also be used to maintain its orientation and avoid asymmetric gravitational effects on the internal flow.

Embodiments of the invention may allow positioning the entire ultrasonic system, e.g., transducer 105 outside the fluid volume with no contact with the sample. In such case the acoustic power and the return signal may propagate through the wall of the test vessel. This may be arranged if the wall of chamber 113 allows the propagation of sufficiently high levels of ultrasonic energy through it to generate acoustic streaming within the sample (when necessary) and to allow generation of an adequate backscattered signal from the moving particles that may propagate back across the wall for detection. Such through-wall systems may be used for example where aseptic conditions are required.

In order to minimize the amount of dissolved gas in sample 112, sample 112 may be heated to a desired temperature, for example, 37° C. and may be held at that temperature for one hour or other period of time. Furthermore it may be then cooled rapidly to a lower temperature, for example, 24° C. before measurements are taken. During the measurements sample 112 may be held at the lower temperature. Any other temperatures and/or periods of time may be used, and heating and cooling may not be used.

System 100 may include transducer 105 which may have for example a resonant flat piezoelectric ceramic crystal and concave elastomeric focusing lens. Other transducers, for example, transducers with shaped piezoelectric elements to create focusing may be used. The resonances, while not very sharp, may be used to maximize the transmitted signals and the reception sensitivities. Transducers may have different diameters and focal lengths, such as for example, 4 mm and focal lengths of 1.6 mm, and an outer diameter of 6 mm and focal lengths of 7 mm. For example, if the focal length of the transducer is on the order of 1.6 mm, the focal volume or focal zone in the vicinity of the focus may be on the order of a cubic millimeter. Any other suitable transducers with any diameters and focal lengths may be used.

A method according to embodiments of the invention may be simple or minimally invasive as it may require a single transducer 105 in acoustic contact with the sample to both launch the interrogating signal and receive the backscattered signals. Any number of transducers may be used. This may not require physical contact with sample 112. Test chamber walls 113 may be acoustically transparent and transducer 105 may be placed outside sample 112 volume. This may be desirable when aseptic conditions are desirable.

Transducer 105 may be for example a pencil type employing a flat piezoelectric crystal with a convex rubber lens to focus the ultrasound energy to a small volume in which large power densities and ultrasonic field gradients are produced. Any other type of transducer that may generate an adequately large ultrasonic pressure signal in the fluid may be used. In one embodiment a focused transducer may be prescribed so that the bulk of the backscattered energy is generated in a small focus volume. This allows the system to be used in a variety of test volumes as long as there are a sufficient number of particles moving through that volume to allow the measurement. Transducer 105 may be inserted into the side of the test chamber 113 through for example a hole or other opening.

The fluid and particle streaming may be a flow away from transducer 105 which may be generated by for example the radiation pressure of the interrogating acoustic energy on the fluid of sample 112. It and the resulting backscatter may be enhanced by the high levels of acoustic energy in the focal volume due to the large acoustic field there which may be produced by for example focusing. This energy may also be confined to a small frequency range by the use of narrow band interrogating signals, and the power spectrum of the interrogating signal will be strongly peaked at the central frequency of the tone bursts (and also at aliasing frequencies separated from the central frequency by the inverse of the inter-burst repetition rate) This will generate strong Doppler-shifted backscattered signals near (within hundreds to thousands of Hz of) the main peak of the power spectrum. This phenomenon may give rise to movement or velocities of particles in sample 112, and may help stir the fluid. In some embodiments of the invention streaming may allow performance of the Doppler effect measurements without any other source of velocity. Furthermore streaming may allow measurements and analyzing of particle size.

According to one embodiment of the invention when streaming is used as a source of velocity or movement the resulting spectra may show peaks on the order of a few bins wide and hence may represent a very limited velocity range where the resolution in frequency may be measured by the bin width or bin size—the separation in frequency between the successive frequency points. For example, a peak about 10 bins wide may represent a frequency range of 250 Hz and a velocity range of about only 1 cm/sec. These may indicate particle motions at the velocity corresponding to the Doppler shift associated with the frequency difference between these peaks and the main peak representing the interrogating signal. Bigger particles may receive more of an acceleration force by for example the acoustic radiation force, and they may also have greater drag. In some embodiments of the invention bin size may be less than 25 Hz, or in another embodiment, the bin size may be 25 Hz, or in another embodiment, the bin size may be 50 Hz, or in another embodiment, the bin size may be roughly 75 Hz, or in another embodiment, the bin size may be roughly 100 Hz, or in another embodiment, the bin size may be roughly 125 Hz, or in another embodiment, the bin size may be roughly 150 Hz, or in another embodiment, the bin size may reach roughly 200 Hz.

Figure 2:
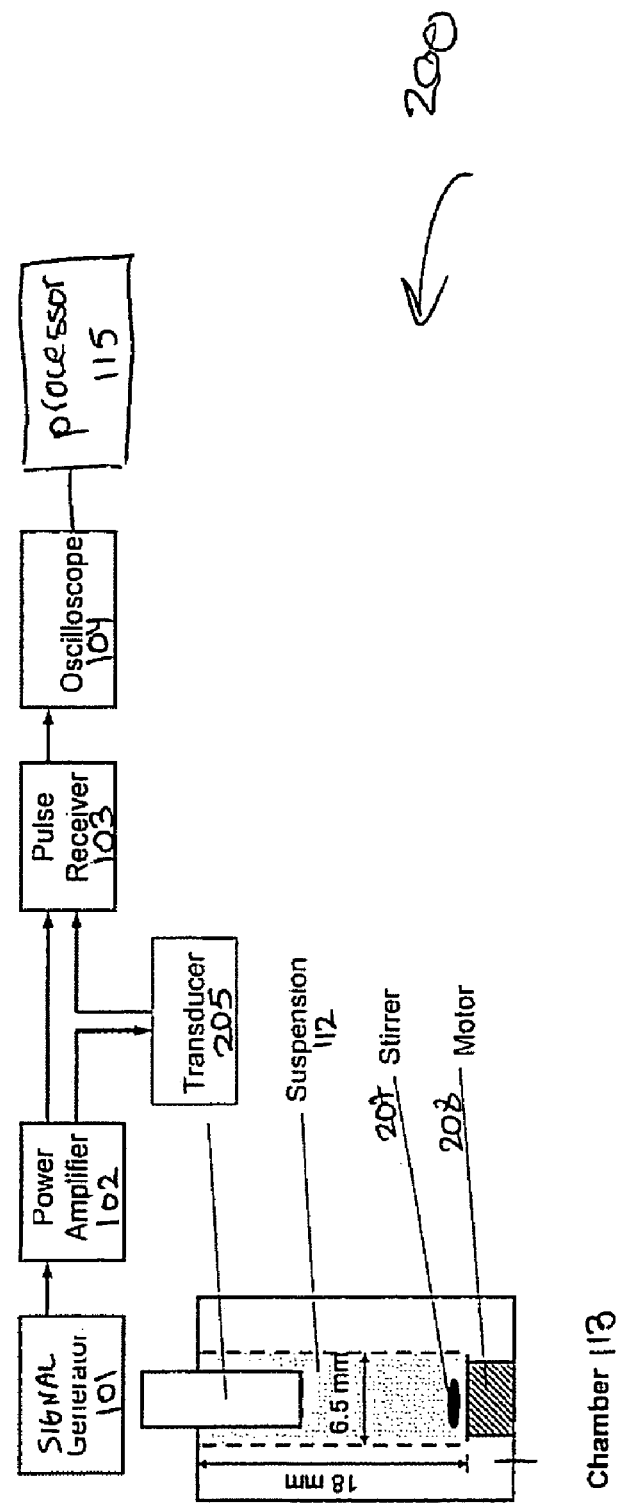
FIG. 2 is a schematic diagram of a system for measuring backscattered power in accordance with an embodiment of the invention.

Another embodiment of the invention may include a vertical transducer as is shown in FIG. 2. Referring to FIG. 2, transducer 205 may be oriented vertically and may enter the chamber 213 from above. The movement or velocities generated by streaming and gravity may tend to add, yielding larger downward velocities directly ahead of transducer 205. Furthermore, with or without stirring, the flow field in the cylinder in this geometry may tend to be downward in the center of the volume and upward around the sides. Consequently, almost all the backscatter sensed by the transducer may be from particles moving away from it in the focal volume. Compared to spectra for measurements with streaming alone, these may have more pronounced structure and greater backscattered power.

System 100 may include signal generator 101. Signal generator 101 may create a signal that is projected into the fluid of sample 112 by transducer 105 (also referred herein as an interrogating signal). The signal may for example include a series of tone bursts, for example, of equal length at the selected center frequency. For example, frequencies between 7 and 20 MHz and tone burst lengths from 20 to 200 cycles may be used. Other frequency ranges and tone burst lengths may be used.

In one embodiment the string of tone bursts of a single frequency may be long, for example, tens of milliseconds while each individual tone burst may be tens of cycles long, or on the order of microseconds in length, repeated every few microseconds. For example, a signal of 40 milliseconds may consist of 5700 bursts of 30 cycles at 16 Mhz, wherein each burst is around 1.9 microseconds in length and repeated every 7 microseconds. In the period in between bursts, also referred to herein as a "gap", the interrogating signal may be turned off. It is in this interval that the signals may return from the focal zone, e.g., the returning signal may be received during the intervals between the tone bursts comprising the ultrasonic signal. For example, the focal zone may be about 1.6 mm from transducer 105, so the two-way travel distance to the zone and back is 3.2 mm, and the leading edge of the signal may return to transducer 105 after ~2 microseconds (3.2 mm/1500 m/sec). The returned, backscattered signal may fall between the tone bursts, where the signal is turned off The signal sent to oscilloscope 104 may consist of the original interrogating signal with the backscattered energy falling between the interrogating-signal tone bursts.

The interrogating signal may be confined to a small bandwidth, for example, on the order of few hundreds Hz. The small bandwidth, and the fact that the signal may be focused in space, may give rise to high acoustic pressures in the fluid in a narrow bandwidth that may drive the streaming and may produce high levels of interrogating signals and backscattered power from islets, cells, and nanoparticles in a narrow bandwidth. This may allow an embodiment of the invention to work with particles which may have weak backscatter.

The tone bursts may be separated in time by a spacing or gap that may be set by several constraints, for example the signal processing architecture and the dimensions of test chamber 113. For example, when a single transducer 105 or 205 of FIG. 2 is used both to direct the signal to the particles and to receive the backscattered return signal it may be necessary that they do not overlap in time, e.g. the backscattered signals may return to the transducer between the tone bursts. The signals may not return before the next tone burst occurs; they may appear, for example, after the tone burst subsequent to one that created them. Thus the separation between the tone bursts may differ from the two-way acoustic travel time to the focal volume in which most of the reflected energy is generated. Another factor in the separation between the bursts may be the distance to stirrer bar 107 when the transducer is working downward into the fluid, for example as in FIG. 2. Energy reflected from the stirrer bar 107 may be received which may include Doppler shifted components that may be distinguished from the desired signal—to coincide with the time of a subsequent tone burst so as not to contribute spurious Doppler shifted energy to the analyzed signal between the tone bursts Inter burst separations from, for example, about 5 to 20 μsec may be used. Other inter burst separations times may be used. For example, signal generator model Agilent 33250A, with an internal trigger, may run continuously in the tone burst mode. In one embodiment, tone bursts of peak-to-peak voltage amplitudes from 10 to 250 $mV_{pp}$ are used, or in another embodiment higher levels are used. Any other suitable signal generator, mode of operation and voltage may be used.

System 100 may further include a power amplifier 102. The tone burst signal may be fed to power amplifier 102 to generate the input signal to transducer 105. The amplified tone burst train may be then sent to transducer 105. For example, power amplifier 102 may be an ENI 607L amplifier which may provide 45 dB of gain. Any other power amplifier providing other adequate gains and interrogating signal levels may be used.

Pulse receiver 103 may be used as a signal amplifier and limiter to prepare signals from power amplifier 102 and transducer 105 for analysis in oscilloscope 104 and processor 115. In some embodiments of the invention processor 115 may be included in oscilloscope 104. Oscilloscope 104, which may for example be operated on a PC or workstation platform under, for example, the Windows NT™ operating system, may also perform the functions of averaging and storing individual spectra. Processor 115 may include components or the functionality of components such as oscilloscope 104, receiver 103, amplifier 102, transducer 105, or a workstation or PC. These preparations may be done by other suitable equipment such as amplifiers, limiters or any other electronic equipment. For example, a Panametrics 5072 PR pulse receiver and a LeCroy Waverunner 6030 oscilloscope may be used. The pulse receiver may provide amplification that may be needed to boost the relatively weak reflected signals, which may be on the order of nanowatts. Amplifications of 40 dB may be used. Any other amount of gain sufficient to produce a signal appropriate for injection into the oscilloscope may be used. Pulse receiver 103 may also be used for limiting its output—the signal input to the oscilloscope, to for example, nominally one volt or 1.5 volt for input to the oscilloscope. This is done on a 'real time' basis, so that the limiting takes place only when the incident signal is present in the signal so that the backscatter signal (between the tone bursts) may be unaffected. This may be significant as the input to pulse receiver 103 may contain the original signal coming from the power amplifier 102 (e.g., on the order of tens of volts) as well as the smaller reflected signals from transducer 105. By limiting the larger signals at their output while amplifying the smaller signals containing the backscatter data, the dynamic range of the signal presented to oscilloscope 104 may be reduced significantly relative to what it may be in the absence of the limiting function. This may be important given the upper limits to input voltage to, and limited dynamic range, for example 8 bits of the A/D conversion in oscilloscope 104.

Oscilloscope 104 and/or processor 115 may be used for digitizing, analyzing and storing the signals received from pulse receiver 103. The analysis may be a calculation of a high resolution power spectrum of the signal containing the incident and backscattered signals with the built in FFT.

The signal processing requirements for the formation of the FFT may be, for example, sampling a 16 MHz signal, which may require a Nyquist sampling rate of at least 32 million samples/sec. The FFT may provide adequate frequency resolution ("high resolution" or "high precision" power spectrum) to produce spectra with adequate detail to capture the spectral shape defined by the fluid flow in the sample. For example, a frequency resolution (the separation between frequency bins in the FFT) may be nominally 25 Hz, 1 Hz, 100 Hz or 200 Hz. Any frequency resolution may be used. The resolution in frequency may be measured by the bin width—the separation in frequency between the successive frequency points. This bin width may be the reciprocal of the length of the signal analyzed. For example, to obtain such resolution, a time domain signal of length 1/(25 Hz)=40 msec may be required. Thus, a typical digitized time domain signal consists of 40 msec of a signal sampled at, for example, 50 MSa/sec, which is a time-domain signal consisting of two million points upon which the FFT is performed. This may require an oscilloscope with memory deep enough to store and operate millions of data points for each FFT. The frequency resolution may go down to 1 Hz, in such cases performing the FFT may take more time. In one embodiment, computation devices provide this degree of spectral resolution with adequate speed, with approximately a 1 second-long interrogating signal. Any other analytical methods other than FFT, such as mixers, narrow band filters and the like that provide adequately high-resolution power spectra may be used.

The high resolution power spectrum may enable the measurement of fluid velocity and particle size in sample 113 when the velocity is generated by streaming. For example, velocities of 1-10 cm/sec correspond to Doppler shifts of 200-2000 Hz at 15 Mhz.

The interrogating signal may be included in the analyzed signal (without the need to gate it out) and may not require the use of special frequency filters to eliminate the non-backscattered signal parts of the spectrum. The latter may appear as the main peak in the analyzed power spectrum. Other embodiments may use time gating or frequency filters to avoid analyzing of the interrogating signal before performing the FFT. One embodiment of the invention may analyze backscatter from any part of the fluid in which it is created by placing the focal zone in the desired part of the fluid. No gating to separate the backscattered energy from that part of the fluid of interest may be required.

Oscilloscope 104 and/or processor 115 may be also used for creating averages of many spectra. Each data point may be the result of the average over 250 individual spectra. The random appearance of very large and broad (in frequency) unphysical spectra, "glitches" or aberrations may interfere with averaging. While the origin of these artifacts has not been determined with certainty, these unphysical spectra have the appearance of spectral leakage associated with Fourier transforms of aperiodic time series. Hanning filters may be provided with oscilloscope 104 software and may be used to suppress spectral leakage. This may be related to the length or the dynamic range of the time series. These artifacts may be removed before the spectra are analyzed (e.g. before averages may be formed). Oscilloscope 104 may also monitor the shape of the spectra as they are computed and only store those that meet specified criteria (e.g, those that represent backscattered energy and contain information about the particles).

One embodiment of the present invention may self-calibrate by measuring the reflected signal from the back wall of the chamber, a target with constant properties. This may be required to assure that the signal generating electronics, e.g., signal generator 101, power amplifier 102 and transducer 105 (in both transmit and receive characteristics) and the signal reception and digitization components, e.g., pulse receiver 103 and oscilloscope 104 are working properly. This may be important when, for example, bubbles may be formed on the transducer lens or acoustic transmission properties of the fluid differ from those anticipated.

When transducer 105 is used on the side of the chamber its normal measurement position may be flush with the wall of the chamber, and since its focal length is smaller than the dimension of the chamber only relatively weak reflections may be seen from the walls. To obtain a strong wall reflection limited in time (e.g. one that may resemble the input tone bursts), transducer 105 may be slid across the chamber so that it may be a fixed distance from the back wall, placing the focal volume near the wall which may be a rigid structure with very high reflectivity. The resulting back wall reflections ("BWR") may be quite large and fall midway in time between the interrogating tone bursts, as is illustrated in FIG. 3.

The BWR may be used as a self-test or may be used to calibrate the system. Such testing or calibration may be performed in for example the time domain or in the frequency domain. For relatively high concentrations, the back wall reflections may not agree with those for lower concentrations, due to the high attenuation or scattering when many particles are present. When this occurs, the BWR signal may be a measure of the attenuation due to the particles and a second measure of the suspension, this time of the forward scattering of the particles. Measuring both the backscatter and the forward scatter may provide more information about sample 112 than just backscatter.

Figure 3:
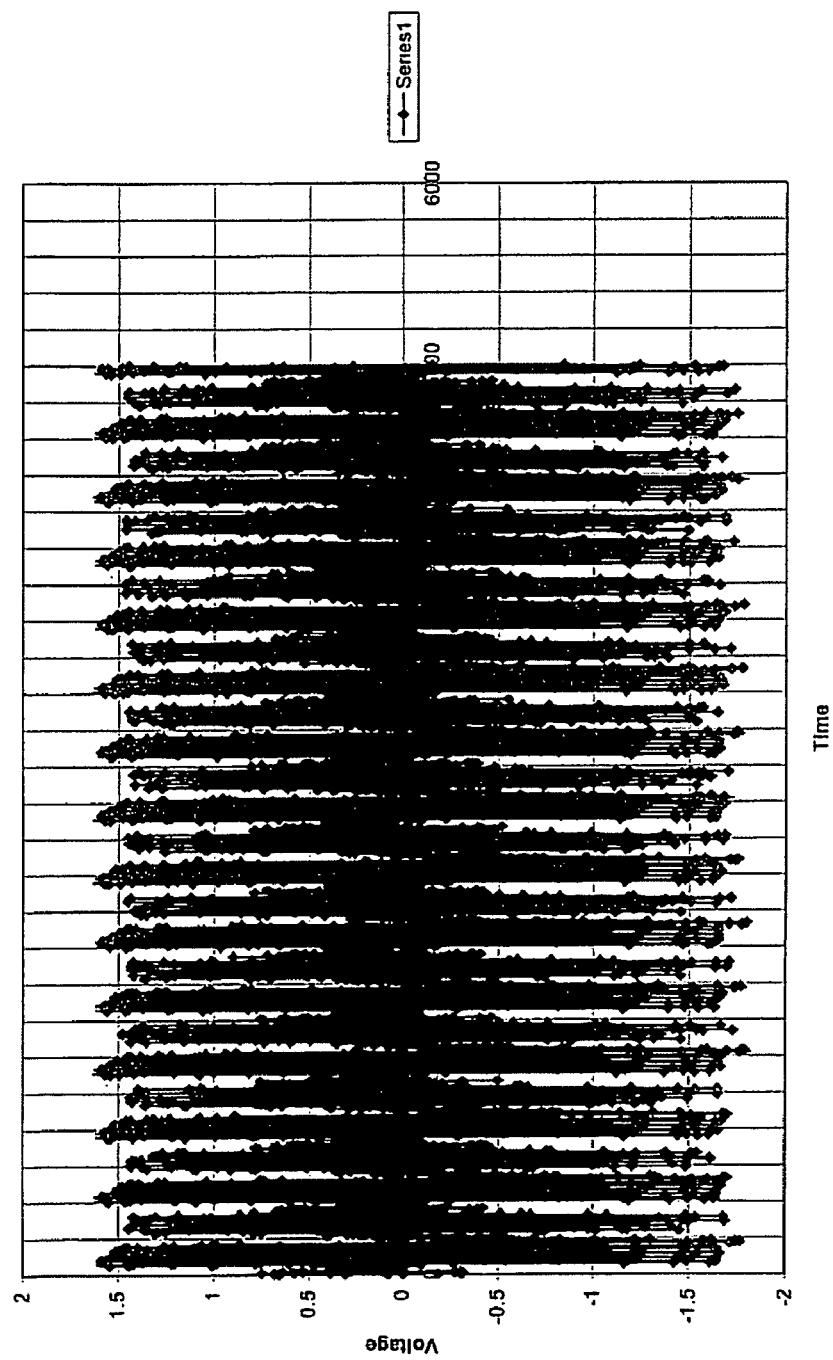
FIG. 3 is a time trace of part of a back wall reflection signal showing acoustic pressure vs. time, according to one embodiment of the invention.

Reference is made to FIG. 3 which shows a time trace of part of the BWR signal showing acoustic pressure vs. time representing main power bursts with the 10-20% smaller reflections from the back wall between them, according to an embodiment of the invention.

The BWR signal at the oscilloscope input may be, in voltage terms, about the same amplitude as the interrogating signal tone bursts. This signal may give a convenient visual reference for the BWR signal which may, for example, if there are no bubbles and the medium is not attenuating the signal, within about 10-20% of the level of the interrogating tone bursts. Usually, if the BWR signal is smaller than expected this fact may be noticed and corrective action may be taken. In the case of, for example, bubbles on the lens, the best approach may be to lower the level of the sample to below the lens and slowly refill chamber 113, stopping when the lens is about half wetted and proceeding very slowly afterward to completely cover the lens. Another solution may be to remove enough of sample 112 to allow removal of transducer 105 entirely from chamber 113 to remove any bubbles from the lens using, for example, a paper towel, and to clean the lens with, for example, an alcohol wipe or by flushing it with water.

The BWR signal may be measured before and after a set of spectra is taken. When there is additional reason for concern, such as, for example, when achieving the anticipated BWR signal was difficult before the start of a measurement, the BWR may be measured several times during data acquisition for a given sample.

Figure 4:
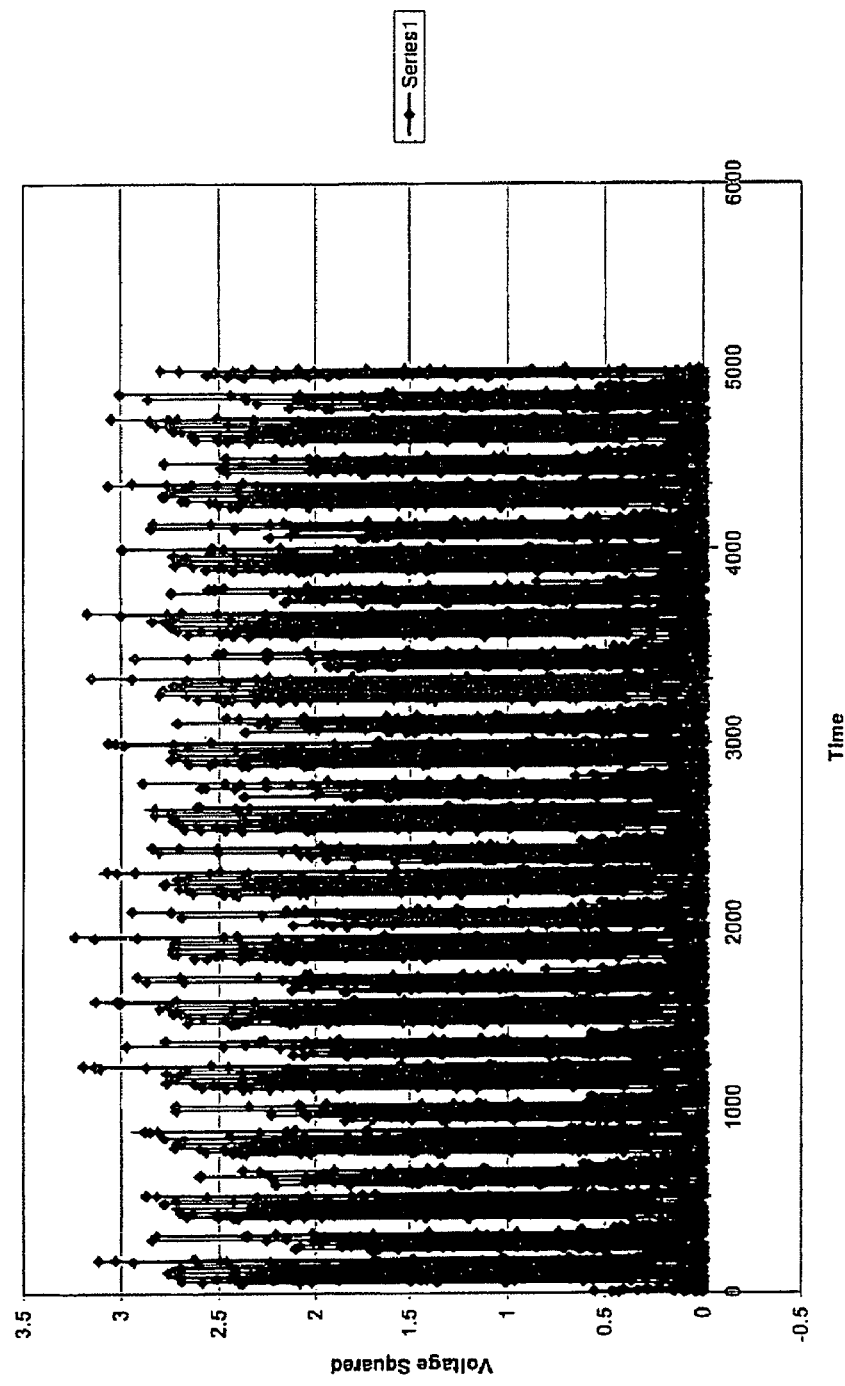
FIG. 4 is a plot of square of a back wall reflection signal, according to one embodiment of the invention.
Figure 5:
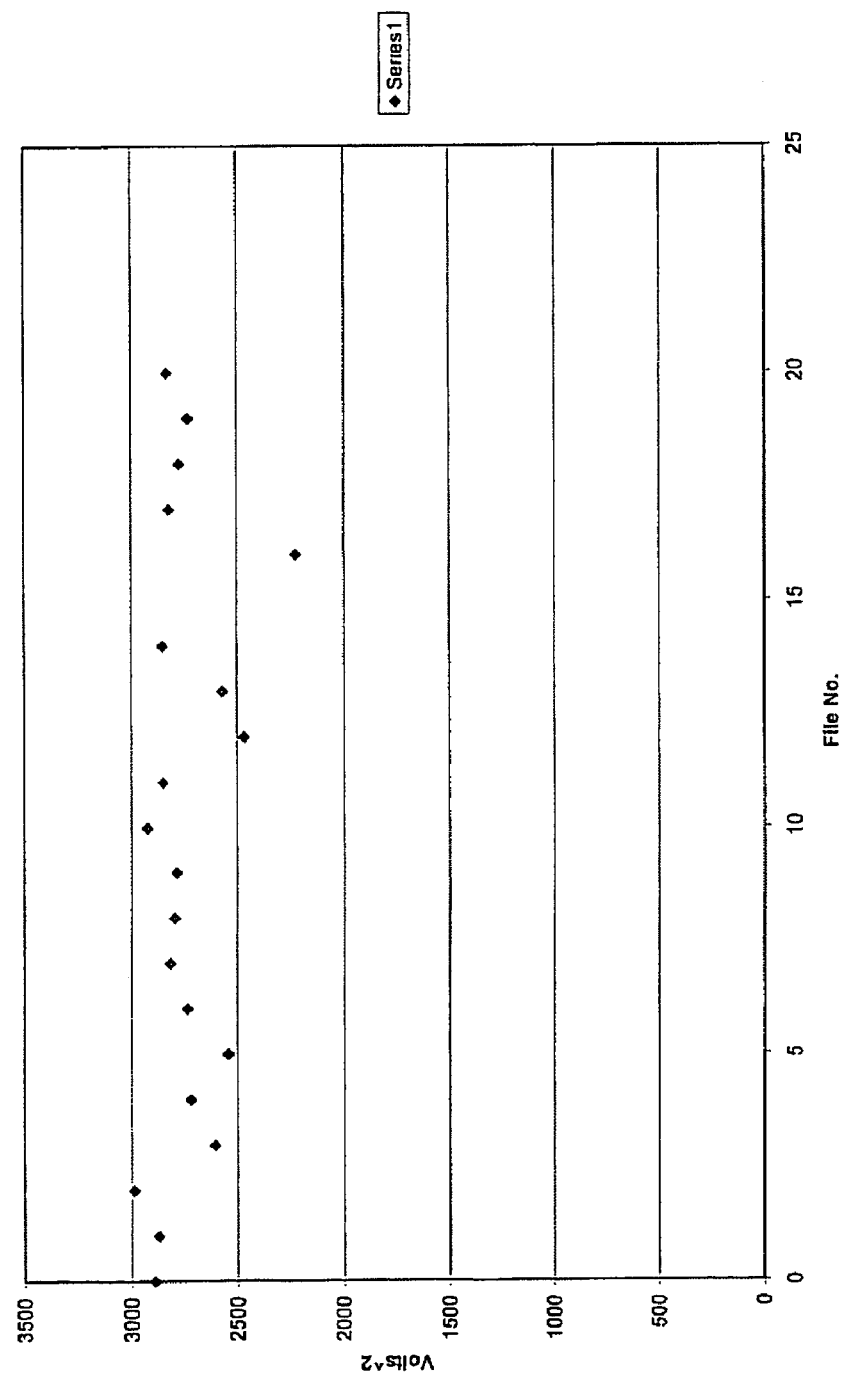
FIG. 5 is plot of back wall reflection coefficients for measurements of 20 human islet samples, according to one embodiment of the invention.

Reference is made to FIG. 4 which shows a plot of the squares of the voltage of a BWR signal used to calculate BWR coefficients, according to an embodiment of the invention. A quantitative measurement of BWR may be obtained from a BWR time trace signal This BWR coefficient may be obtained by isolating a portion of the BWR signal (e.g., 4,000 points representing about a dozen tone bursts and back wall reflections between), and summing the squares of the voltage at every point and separately adding the sums in the tone bursts and in the wall reflections to obtain measures of power in each. A plot of these squared time series is shown in FIG. 4, and a comparison of this BWR metric for a series of measurements is shown in FIG. 5

In cases when the sample's acoustic properties vary from that of water, for example, in samples with very high concentrations there may be substantial attenuation of propagation of acoustic waves or if the sample has an acoustic impedance that differs significantly from that of water the acoustic pressure generated in the medium may differ from that in the chamber when the reference BWR signal was defined. In such cases, the deviation from the reference BWR coefficient may be a function of the concentration and this deviation then may provide a second and independent measurement of the concentration. Other ultrasonic concentration measurement methods may be based on such differences.

Figure 6:
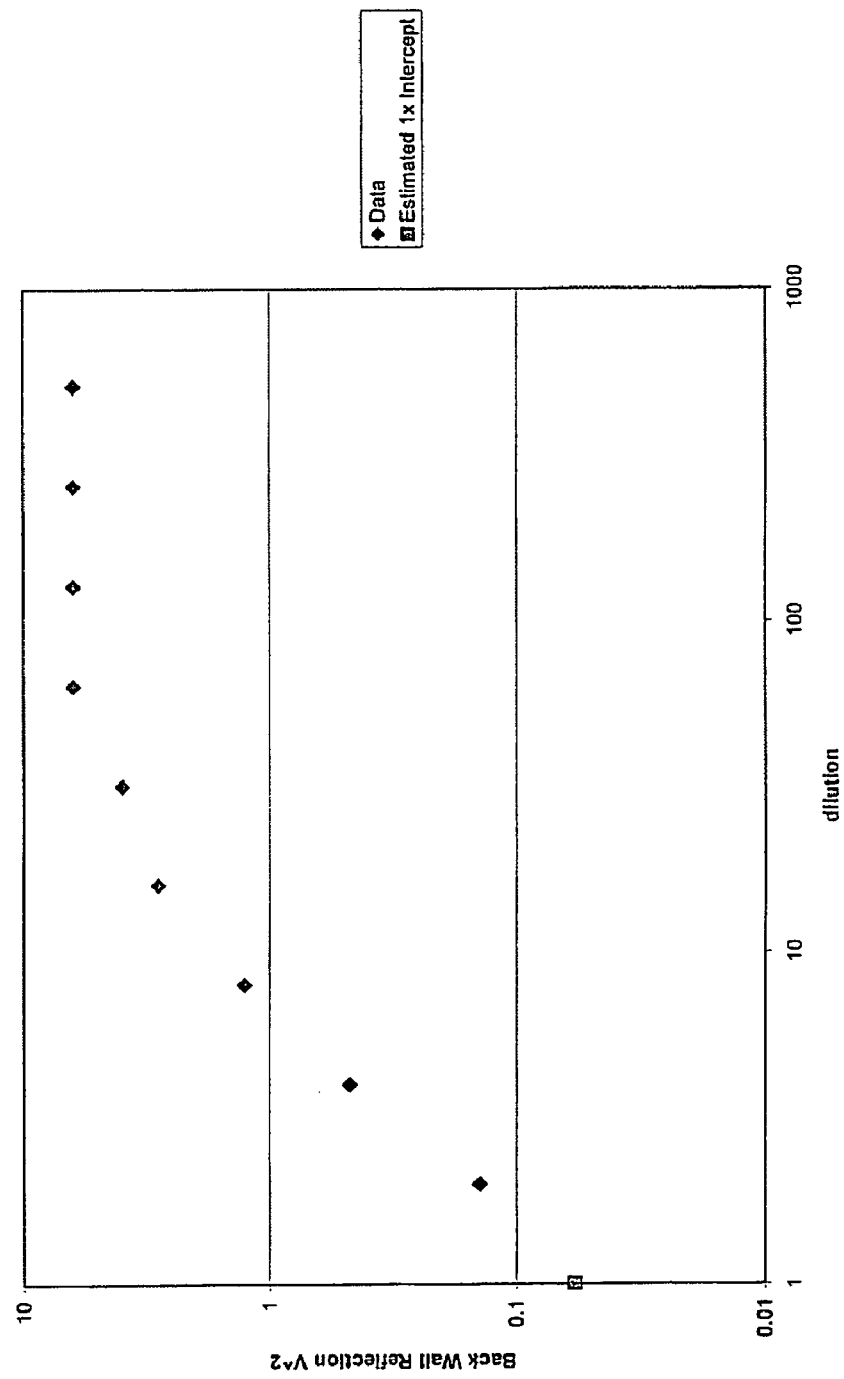
FIG. 6 is plot of a back wall reflection signal measured with perfluorocarbon particles in an emulsion, according to one embodiment of the invention.

Reference is made to FIG. 6 which shows a BWR signal measured with perfluorocarbon particles in an emulsion to decrease with increasing concentration, according to an embodiment of the invention. The BWR is shown as a function of dilutions in a perfluorocarbon emulsion. The original undiluted sample (dilution of 1) has concentration 40% by volume. As the samples are diluted concentration may decrease and the BWR may increase until it reaches the level comparable to that found in water.

Attenuation may reduce the backscattered energy per unit concentration reaching the transducer and may cause a calibration curve to deviate from linear at higher concentrations. BWR signals may provide a measure of the attenuation which may be used to construct a normalization function to "correct" the concentration vs. reflected power curves and may allow construction of a linear calibration curve to concentrations above the regime in which the effects are small.

Development of a calibration curve representing backscattered power vs. concentration may require precise knowledge of the concentration of measured samples. In one embodiment of the invention establishment of the concentration of a sample may be done by removing the entire sample from the measurement chamber after acoustic measurements are made and then to determine its concentration by independent means. For biological samples, for example, this may entailed lysing the cellular materials and counting nuclei in the Guava cell counting apparatus. This may eliminate any uncertainties due to for example pipeting.

Figure 7:
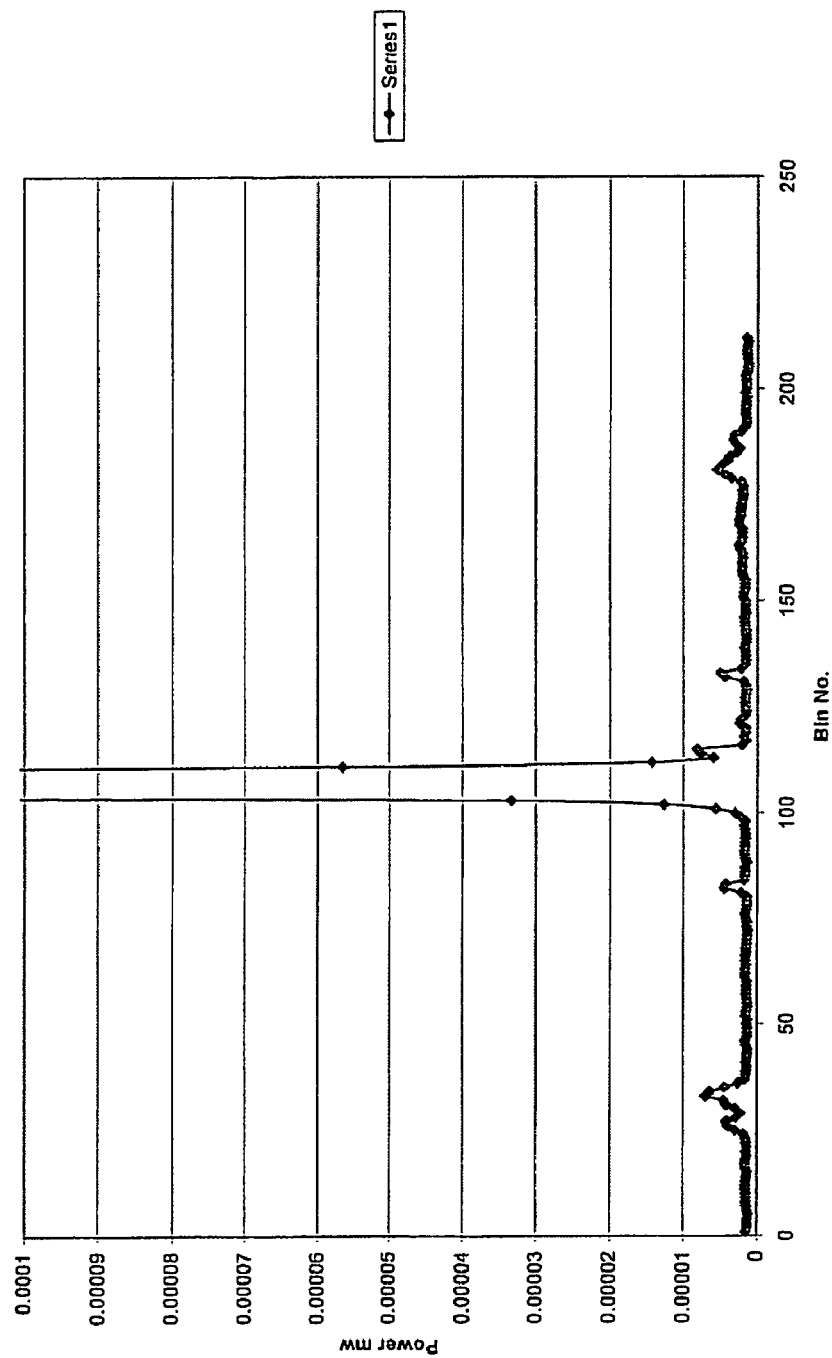
FIG. 7 is an average spectra for human islet data taken without stirring, taken as a background measurement, according to one embodiment of the invention.
Figure 8:
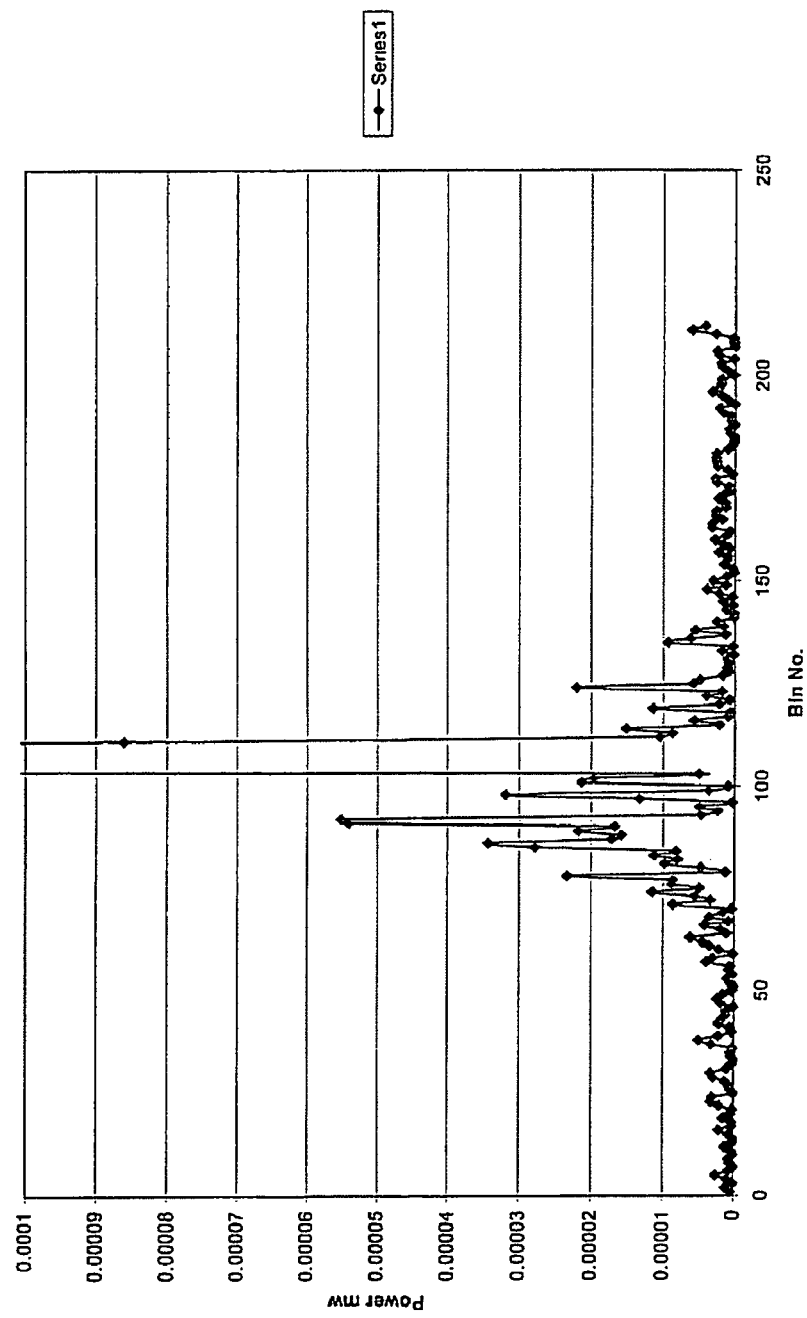
FIG. 8 is an individual spectrum for perfluorocarbon emulsion without stirring, according to one embodiment of the invention.
Figure 9:
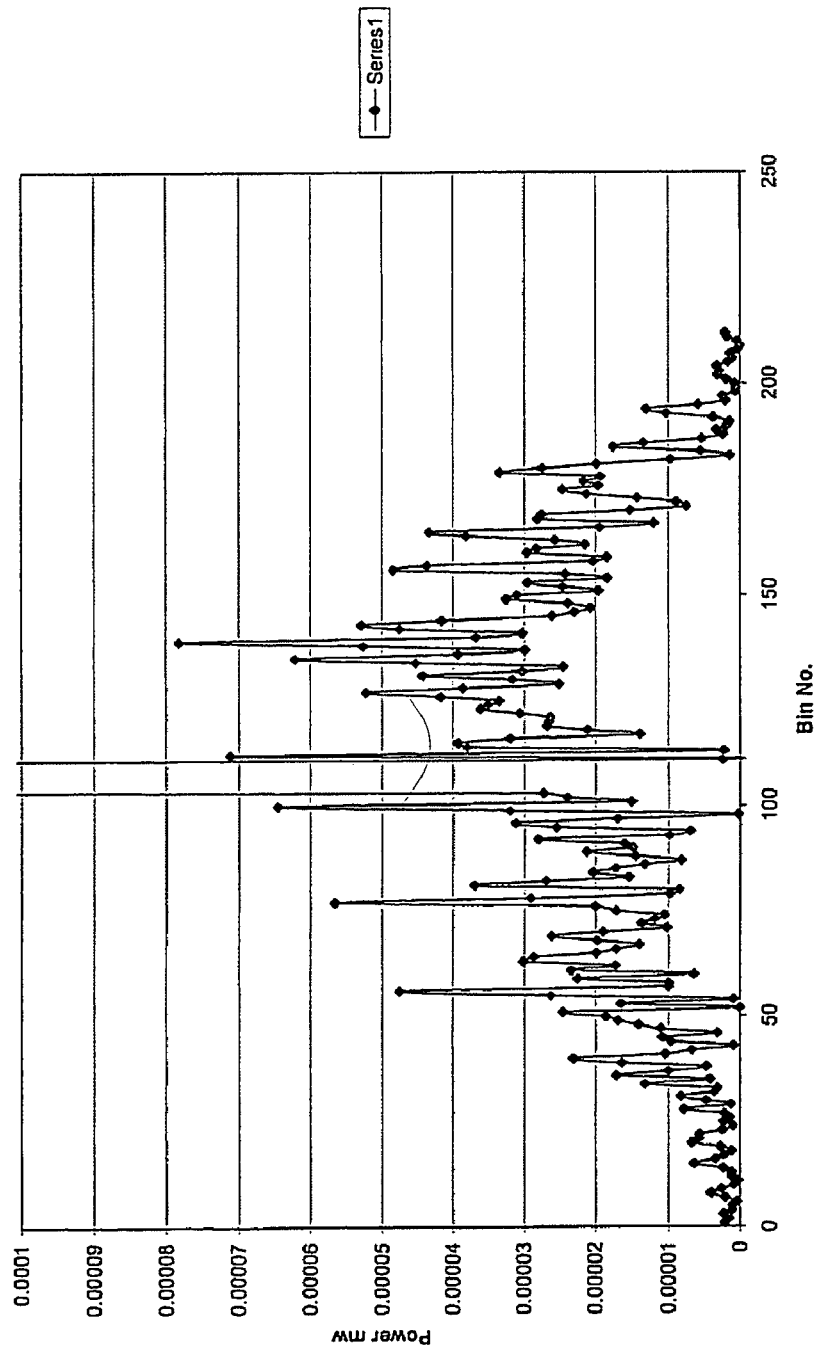
FIG. 9 is an individual spectrum for 548/ml suspension of human islets with stirring, according to one embodiment of the invention.

Reference is made to FIGS. 7, 8 and 9 which show the high resolution power spectra of the backscattered signal which is a basic unit of data, according to an embodiment of the invention. These spectra may contain for example 212 frequency bins separated by 25 Hz. All spectra show a large central peak, for example, about ten bins wide on this scale at the main frequency (e.g., 16 MHz in this case) which may represent the voltage-limited version of the signal driving transducer 105. The background spectrum has a flat shape on either side of the main peak at around 0.000002 mw or 2 nw in the 25-hz wide spectral bins. Other sizes and frequency ranges may be used.

FIG. 7 shows average spectra for human islet data taken without stirring, taken as a background measurement as the Islets may have sunk to the bottom of the test chamber in the absence of stirring and may not have been counted, according to an embodiment of the invention. Small humps in the spectra may be due to electronic spurs FIG. 8 shows an individual spectrum for perfluorocarbon emulsion without stirring, according to an embodiment of the invention. An elevated "hump" between bins 75 and 100 may represent reflected energy from particles moving away from the transducer due to streaming at about 2 cm/sec (at the center of the hump).

FIG. 9 shows an individual spectrum for 548/ml suspension of human islets with stirring, according to an embodiment of the invention. There are elevated regions on either side of the main peak which may represent the continuum of particle velocity components toward and away from the transducer due to, for example, the rotational motion of the particles due to stirring. Individual spectra of this type may be symmetrical or asymmetrical about the main peak while averaged stirred spectra may tend to be symmetrical. When there is a large component of streaming in addition to stirring, the left side of an averaged spectrum may be elevated relative to the right indicating enhancement of the signal on the left due to acceleration of particles moving away and a suppression of the signal to the right due to a deceleration of particles approaching the transducer.

Each spectrum may be characterized by the backscattered energy contained in its off-peak bins. This energy may be estimated by a simple bin by bin power sum. For example, the power in the n-th bin is first converted from Power Spectrum level in dB $P_{dB-n}$ to its linear value by the conversion $P_n = 10^{(PdB-n/10)}$, and the power sum may be formed. For an asymmetrical spectrum with a hump on the left hand side, a sum of the form of equation 1 may be used:

$$P_{backscattered} = \sum_{n=n_1}^{n_2} P_n \qquad [1]$$

where the energy in the hump is between bin numbers $n_1$ and $n_2$. Other suitable equations may be used. For example, $P_n$ may be replaced by $(P_n-P_{background})$ where $P_{background}$ may represent the background value of power with no particles present. In this formulation, the backscattered power automatically tends to zero in the absence of particles. The total power may be this sum of spectral levels times 25 hz, or 25 $P_{backscattered}$.

For symmetrical spectra, where the energy of reflections may be found on either side of the main peak, a double sum may be used, for example, as the sum of equation 2:

$$P_{reflected} = \sum_{n=n_1}^{n_2} P_n + \sum_{n=n_3}^{n_4} P_n \qquad [2]$$

where $n_1$ may represent the lowest bin included in the sum, $n_2$ may represent the last bin counted before the spectrum peak, $n_3$ may represent the first bin counted to the right of the main peak and $n_4$ may represent the highest bin counted. This may be equivalent to assigning all the input energy (the main peak) to the bins between $n_2$ and $n_3$ and backscattered energy to the bins above and below these. Any other formula, equation or calculation may be used for characterization and/or estimation of the spectrum. The powers $P_n$ may be replaced by $P_n-P_{background}$ to obtain a quantity that may tend to zero in the absence of particles. As above, the total power may be this sum of spectral levels times 25 Hz, or 25 $P_{backscattered}$ Optimization of bin selection may be a function of the measurement (e.g. for higher input voltages the main peak may be somewhat wider). For example, the main peak may be assigned to bins 100-113 and may be summed over the entire remaining bins (i.e. $n_1=1$, $n_2=99$, $n_3=114$ and $n_4=212$). These power sums may be on the order of several hundred to several thousand nanowatts.

The same sums may be computed for background spectra (e.g., with no particles present or with the stirring turned off so that the particles fall to the bottom of the measurement vessel) and the power so obtained may be subtracted from the power with particles to form concentration calibration curves that approach zero for concentrations approaching zero.

There may be a wide variability in these spectra for a given sample. Some may be very close to the background, and may be indicative of little backscatter during the analysis time window, and others may show much higher backscatter and definite structural shape in the spectra. There may be also a large range in the associated power. The statistics of this variation may be driven by the variation in the number of scatterers that contribute to the power in a particular spectrum. The power may tend to follow a log normal distribution.

A spectrum may include a very large feature such as for example a large peak to the left of the main peak which may indicate scattering from a large object moving away from the transducer. This may indicate, for example, the presence of clumps of sample material or a foreign object or air bubble in the sample or the like. Appearance of several spectra of this type may require further study of the sample.

As described above, about, for example, 10% of the calculated spectra may not have this character. These may have very wide main peaks, and the general levels may be one or more orders of magnitude larger than the majority of the spectra. Such spectra may be artifacts, most likely the result of spectral leakage due to, for example, a failure of the Hanning filter used to condition the very long time records for the FFT. Identifying these electronic "glitches" may be done by using a main peak width criterion. Any other method of identifying may be used. This may identify spectra with main peaks that may be broader than about, for example, ten frequency bins when plotted with, for example, an ordinate of 0.0001 mw as unphysical. Almost all "glitch" spectra may fail this test by a wide margin and may be eliminated from analysis. However, there may be a small number of spectra that may not readily be assigned to either the data or glitch category and because these may tend to contain power that is relatively high with respect to the rest of the data, for example, two or more may affect a measurement by a few percent.

It has been found with one embodiment and one set of data that no artifacts or "glitches" occur for operations at 20 MHz with the existing electronics which is a strong indication that these are indeed artifacts arising in the signal processing.

After the FFT's are taken and stored in the oscilloscope they may be imported to a mathematical tool, for example, an Excel™ file or other suitable mathematical processor and the indicated power calculations may be performed for each spectrum. The power from the FFT's may be plotted as a function of spectrum number, as shown in FIG. 10.

Figure 10:
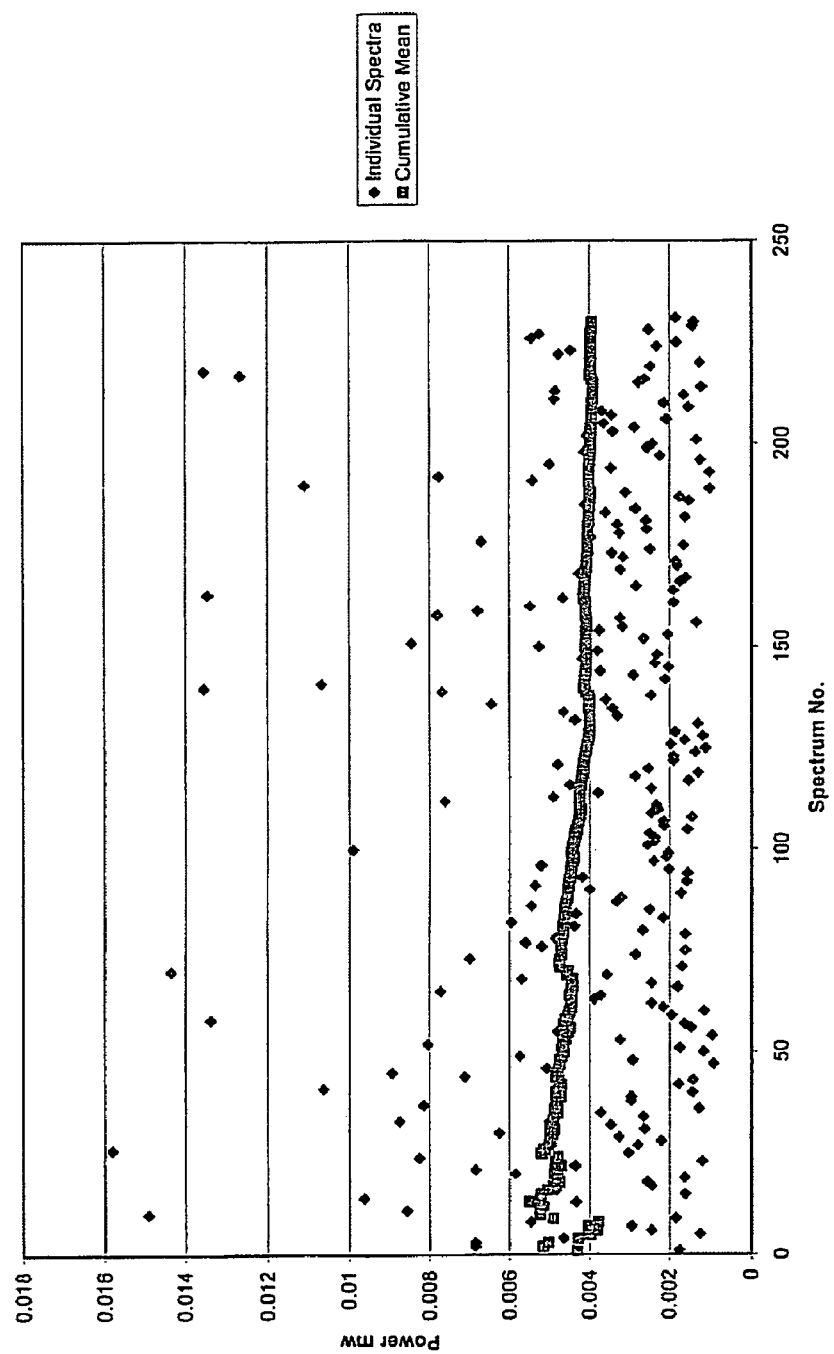
FIG. 10 is a plot of a "cloud" of spectral power for human islet measurement and cumulative mean curve, according to one embodiment of the invention.

FIG. 10 shows a "cloud" of spectral power for human islet measurement and cumulative mean curve, according to an embodiment of the invention. Cumulative mean is flat after 125 points, indicating a stable measurement. In this example, "glitch" points have been removed. There remains, however, a fairly large range of powers between the mean of around 1500 nw/25 Hz and the largest values around 12,000 nw/25 Hz.

The second curve on FIG. 10 is a cumulative mean of the spectra, according to an embodiment of the invention. Each point on this curve may represent the mean of the backscattered power for all the spectra to its left. The final value may be the average over the entire set of spectra and may be the final reflectivity value for this measurement. The slope of this cumulative mean curve may be a measure of the stability of the measurement If the measurement represents a steady state condition with a converging mean this curve may be flat; that is, there may be no change with increasing numbers of spectra. The cumulative mean may show large jumps as it incorporates higher-power spectra, especially toward the beginning of run where there are fewer spectra included in the average. Very large jumps may indicate non-physical data.

When high energy spectra that may be difficult to assign to either artifact or "real data" status may occur, their effect on the cumulative mean may be estimated by calculating it with and without them. This may be a measure of the precision of a measurement. In another embodiment automated criteria may be used to sort the spectra in terms of the total measured backscattered power to eliminate operator bias. In this embodiment, the spectral power assigned to a measurement may be the average power for, for example, the lowest 200 of 250 spectra. Other embodiments may be designed with electronics and signal processing that may eliminate these glitches.

For each data point an average spectrum may be computed by, for example, taking the bin by bin average for all spectra included in the analysis for that measurement point. These spectra may be smoother and easier to interpret than the individual spectra, which may not smooth and vary greatly one to the next. Average spectra for the data from which the individual spectra shown in FIGS. 8 and 9, not stirred and stirred, were taken are shown in FIGS. 11 and 12.

Figure 11:
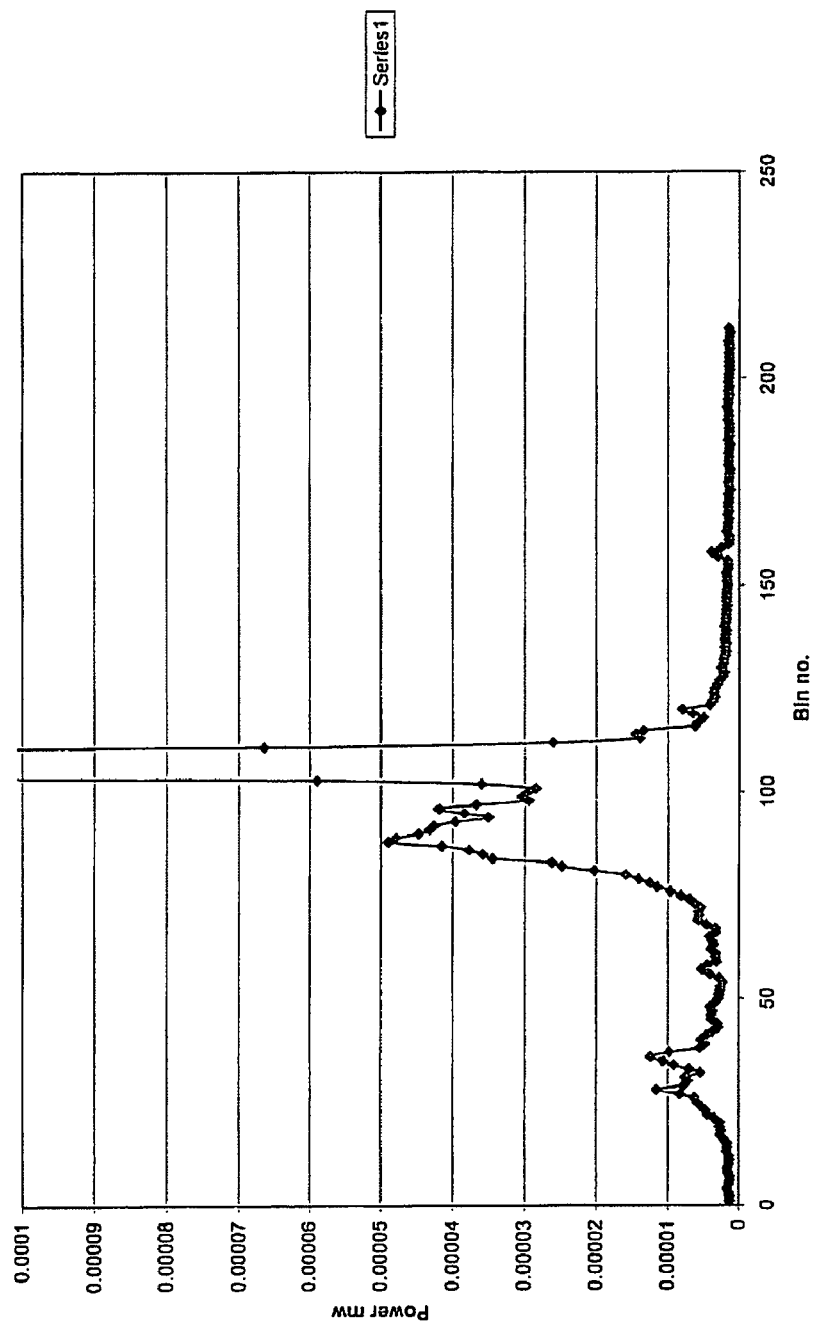
FIG. 11 is an averaged spectrum for a relatively high concentration of a perfluorocarbon emulsion measured without stirring, according to one embodiment of the invention.

FIG. 11 shows the averaged spectrum for a relatively high concentration of a perfluorcarbon emulsion measured without stirring, according to an embodiment of the invention. Two humps appear centered about 20 and 75 bins from the main peak, corresponding to 500 and 1900 Hz below the center of the main peak. These may represent particles moving away from the transducer with acoustical-streaming-induced velocities on the order of 2 and 8 cm/sec. This may suggest the presence of two different species in the sample.

The spectral cloud data for this measurement may also suggest this, as the last twenty or so spectra were elevated with respect to the previous ones and an average spectrum leaving out these last twenty does not show the lower frequency hump. These data may suggest that a second type of particle migrated toward the focal zone toward the end of the eight minute measurement. Other ranges of frequencies and other bins may be used.

Figure 12:
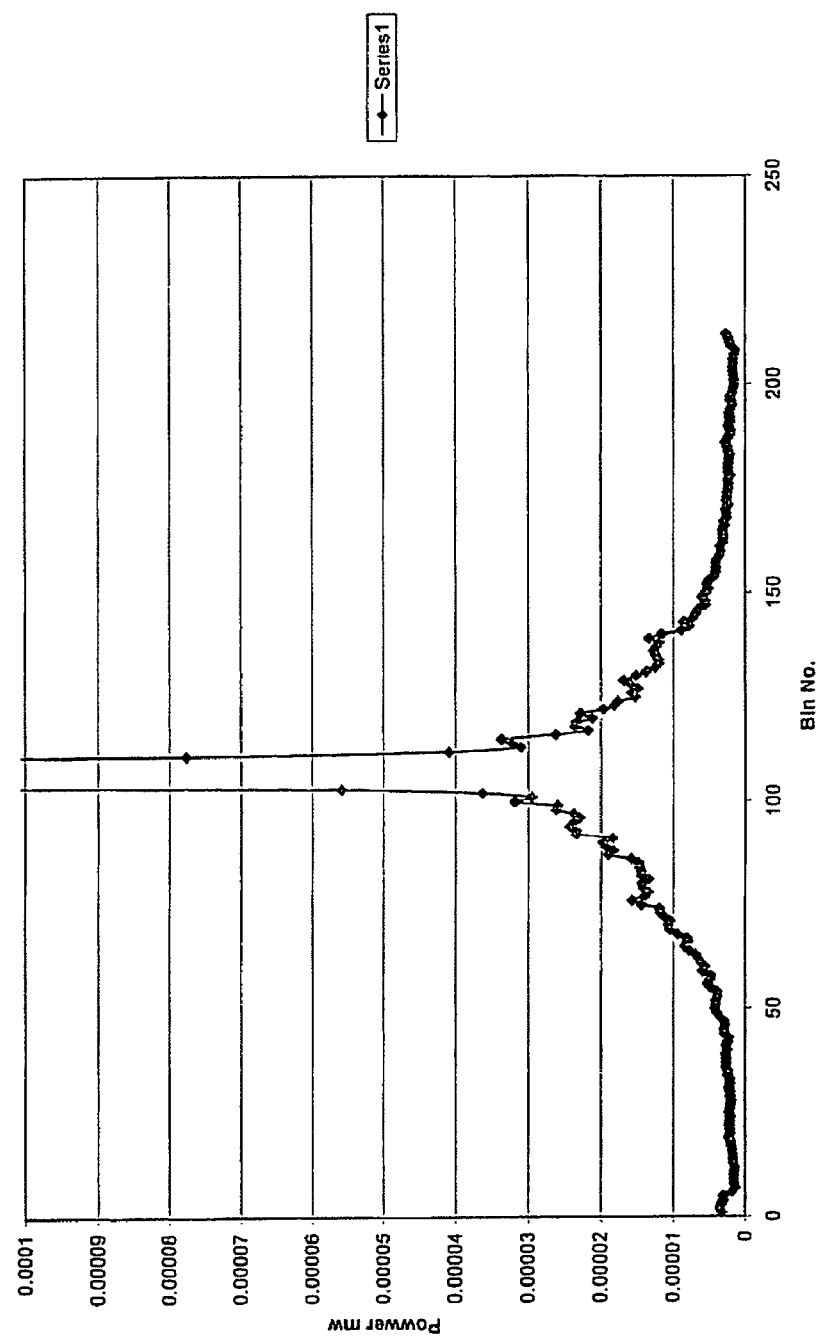
FIG. 12 is an averaged spectrum for 548/ml human islet suspension stirred, according to one embodiment of the invention.

FIG. 12 shows averaged spectrum for 548 ml human islet suspension stirred, according to an embodiment of the invention. This spectrum may be more symmetrical than the individual, and this may be typical of the latter which may tend to show more motion on one side of the peak.

The power sum for the average spectrum may be equal to the average of the power sums of the individual spectra. Therefore it is possible to compute the average reflected power directly from the average spectrum without evaluating the cumulative mean power.

Figure 13:
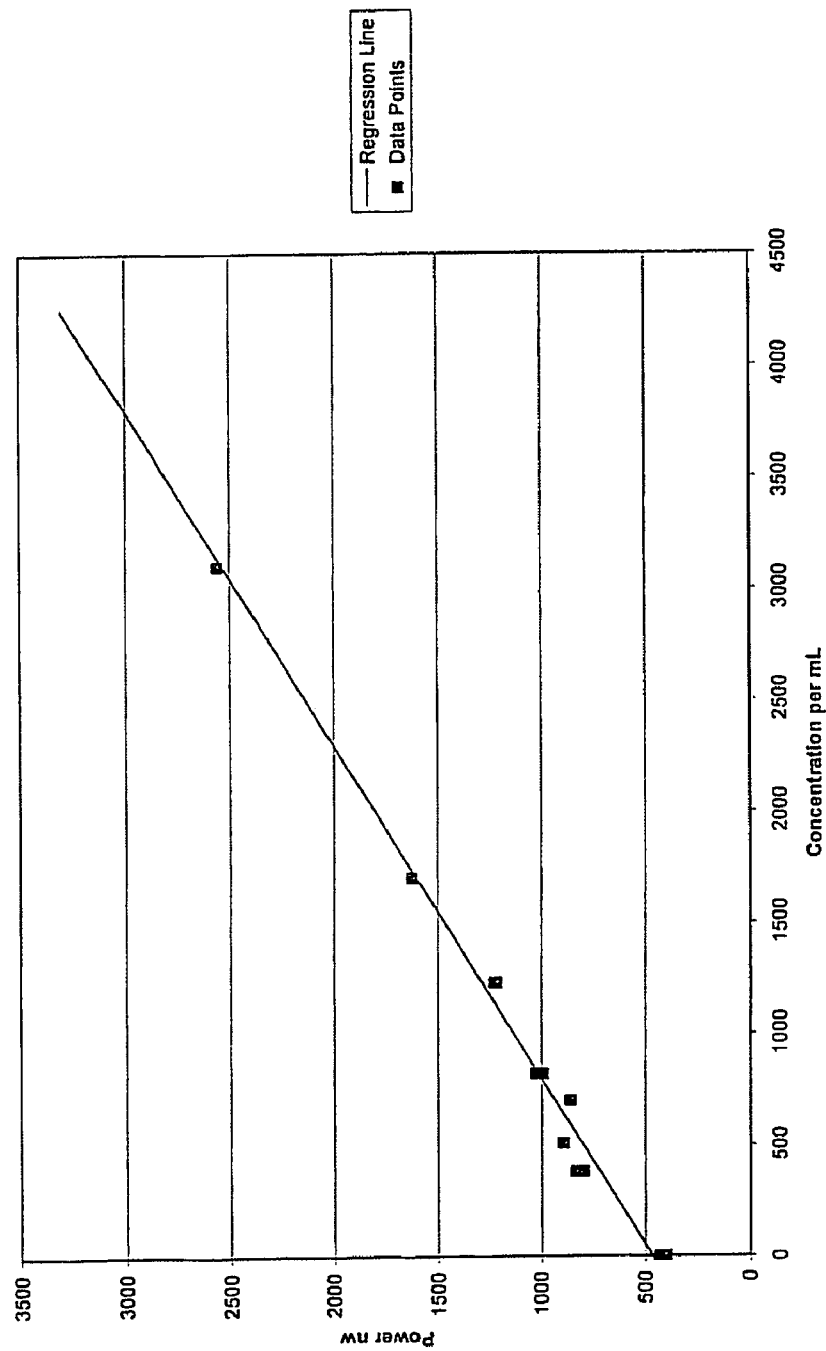
FIG. 13 is a calibration curve for stem-cell spheroids, according to one embodiment of the invention.

FIG. 13 shows a concentration calibration curve taken on murine embryonic stem cell spheroids over several days with the transducer on the side of the chamber, according to an embodiment of the invention. Each sample was lysed and the nuclei counted using the Guava device after the concentration measurement. Lower points near 1700 and 3000 per ml were taken for a set up with slightly depressed value of BWR. In addition linear regression line is shown.

Figure 14:
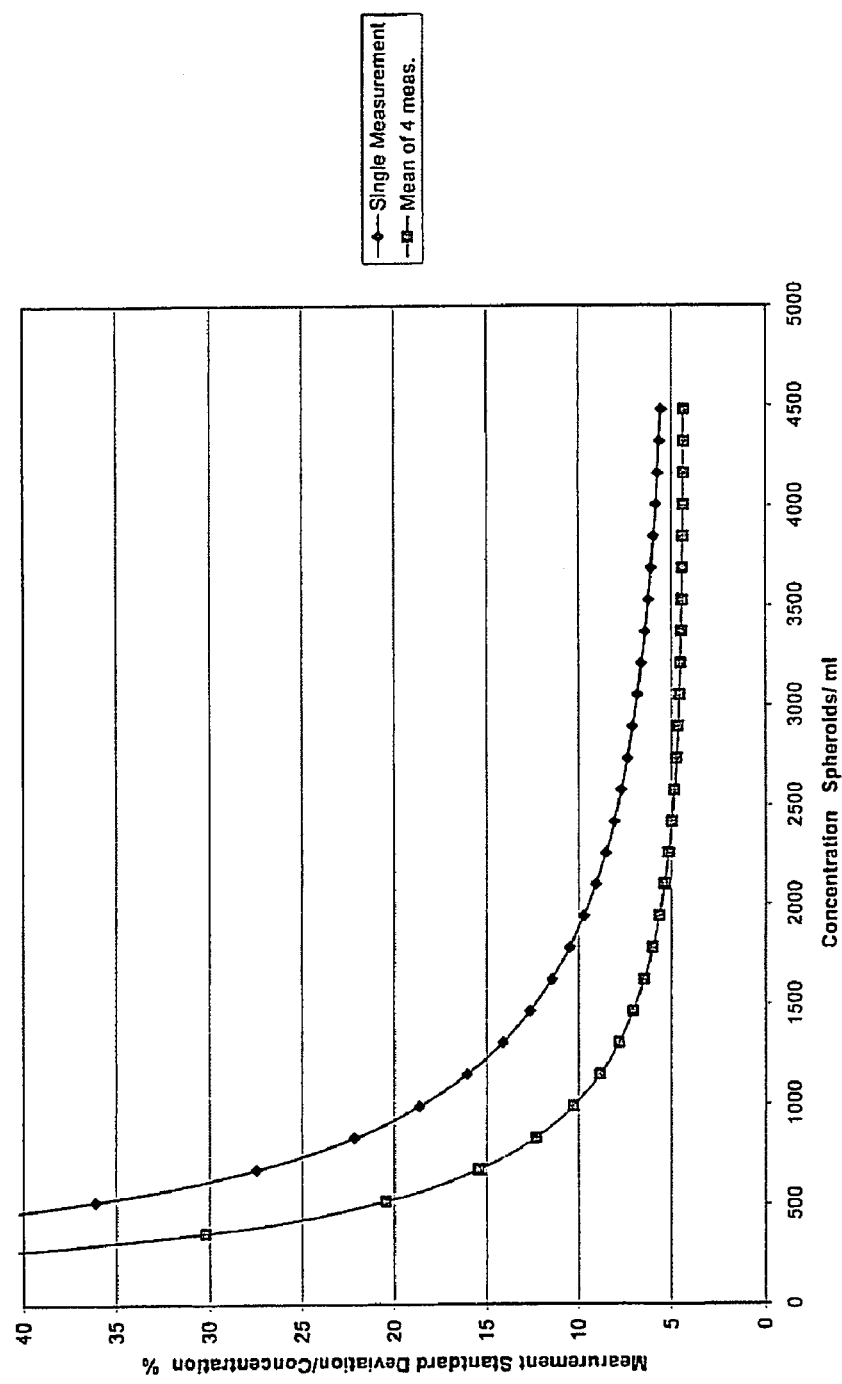
FIG. 14 is a standard deviation of measurement using calibration curve for stem-cell spheroids, according to one embodiment of the invention.

FIG. 14 shows the standard deviation for single and multiple-sample measurements using calibration curve for Spheroids shown in FIG. 13, according to an embodiment of the invention.

Figure 15:
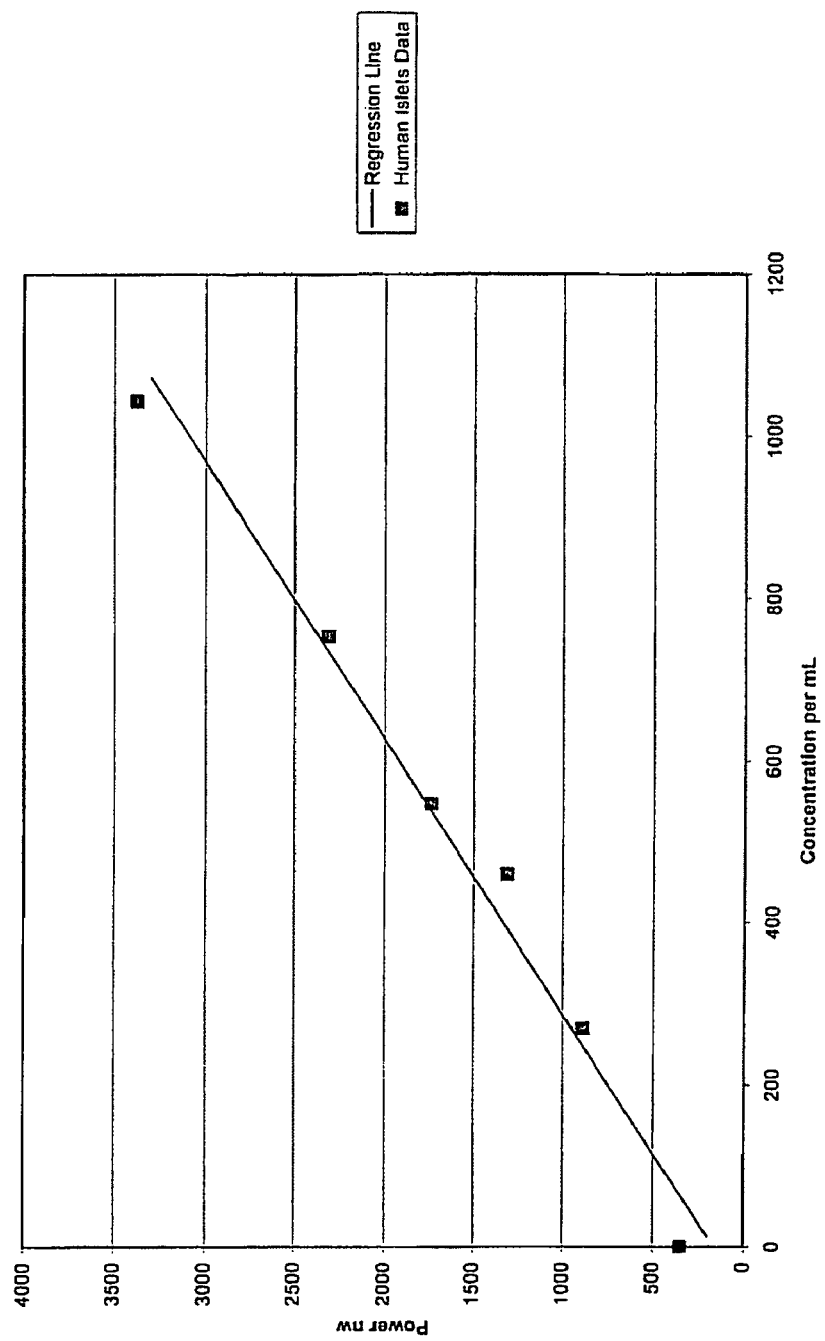
FIG. 15 is a calibration curve for data on human islets preparation and a regression line, according to one embodiment of the invention.

FIG. 15 shows data taken for a very pure preparation of fresh human islets on a single day, according to an embodiment of the invention. Each point represents the average of three sets of 250 spectra (24 minutes of data). The concentration of the original sample was obtained by sampling it and using the nuclei-counting technique. Subsequent lower concentrations were obtained by successively removing 340 microliters of fluid from a sample and measuring the concentration in the removed volume as a measure of that of the sample from which it was removed.

Figure 16:
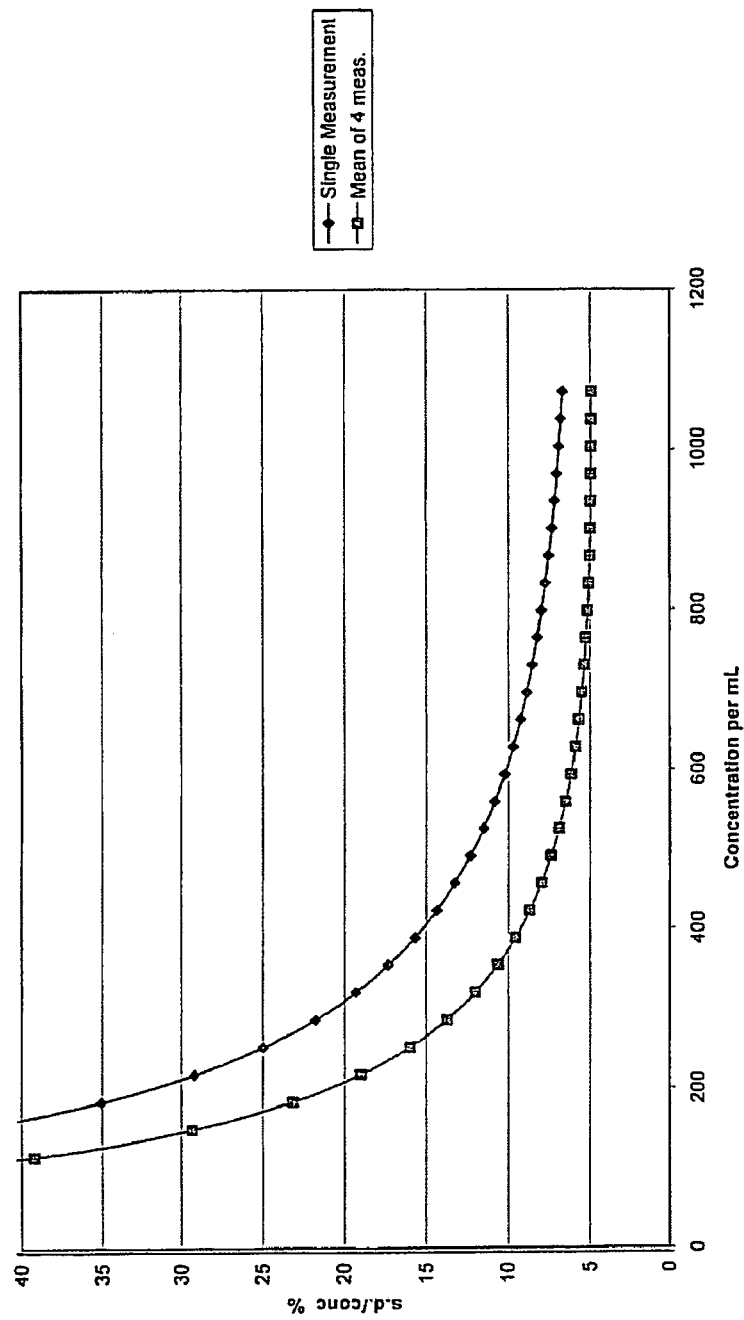
FIG. 16 is a standard deviation of measurement using calibration curve for human islets, according to one embodiment of the invention.

FIG. 16 shows the standard deviation of the calibration curve for human islets shown in FIG. 15 for single measurement, and demonstrates that for multiple measurements, the measurement standard deviation is less than 10% for concentrations at about 400 islets/ml and above, according to an embodiment of the invention.

Figure 17:
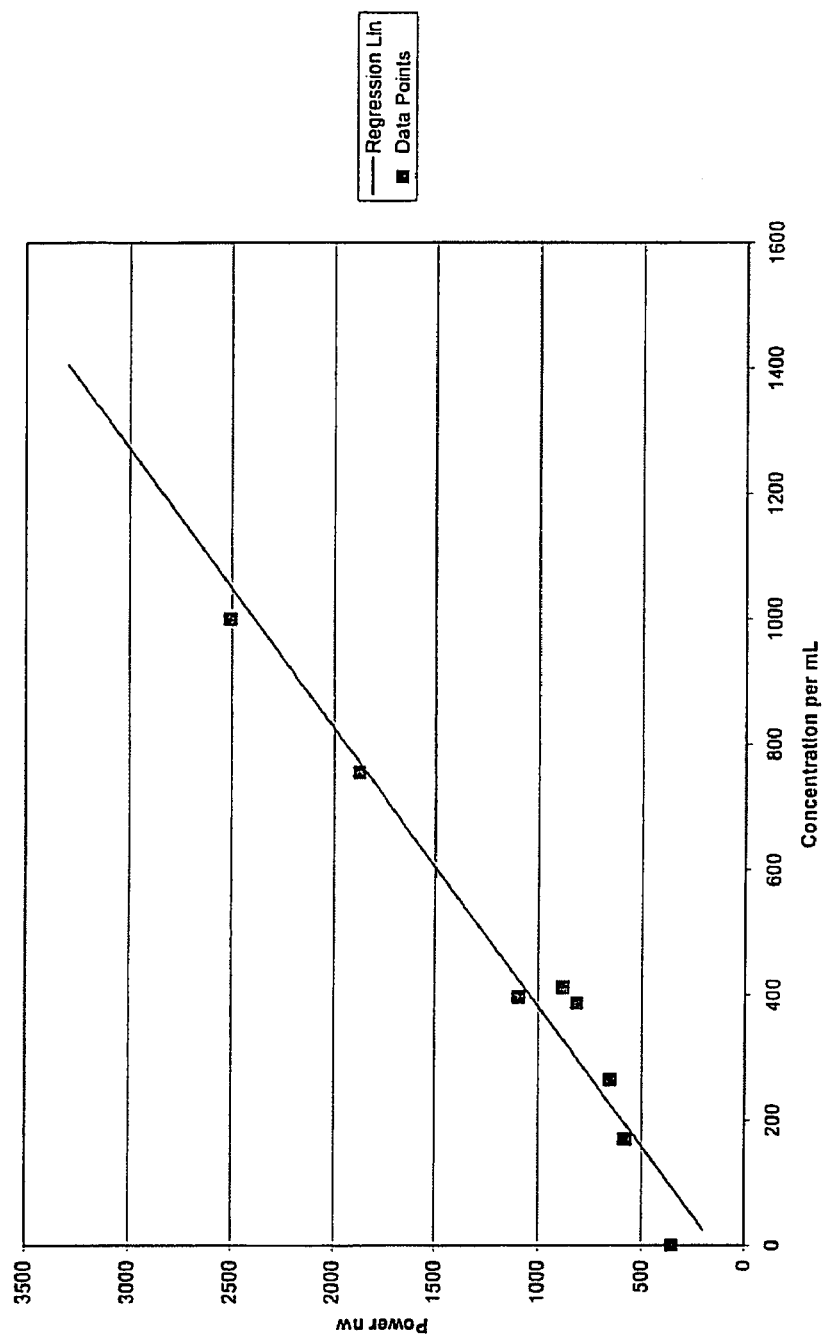
FIG. 17 is a calibration curve for data on exocrine tissue and a regression line, according to one embodiment of the invention.

FIG. 17 shows measured backscattered powers for a comparable range of concentrations of pure human exocrine tissue. These data lie slightly below that for the human islets. The calibration curve is shown with a regression line.

Figure 18:
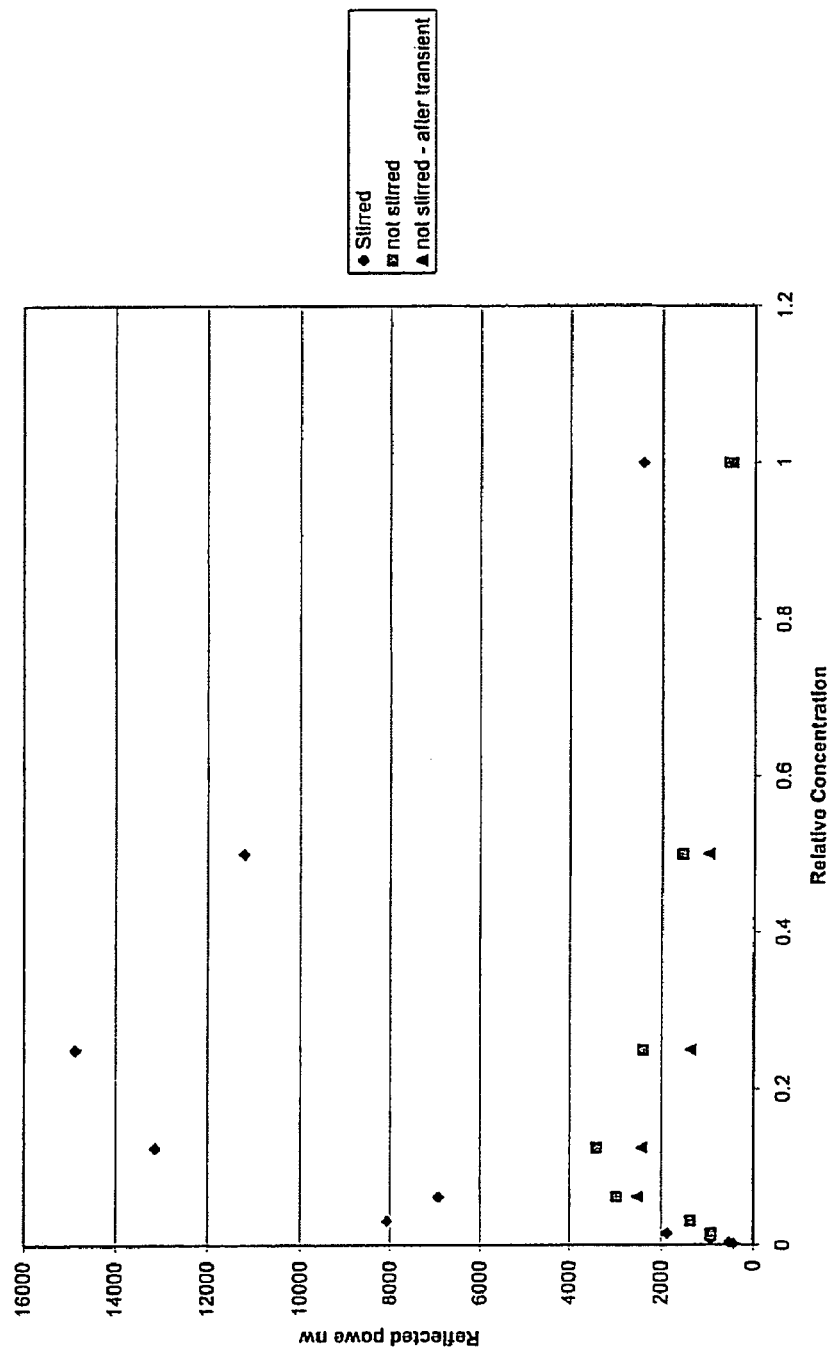
FIG. 18 shows plots of backscattered power and concentration for stirred and unstirred perfluorocarbon emulsions, according to one embodiment of the invention.

FIG. 18 shows backscattered power measurements for samples of a perfluorocarbon pefluorodecalin/Intralipid emulsion, according to an embodiment of the invention. These data show a linear region at low concentrations and a nonlinear region for higher concentrations in which the backscattered power falls below the original straight line and eventually decreases with concentration. The companion curve of the BWR measurements, shown in FIG. 6, shows significant attenuation of the BWR signals at the higher concentrations which is responsible for the reduced reflected power measured at these concentrations.

Figure 19:
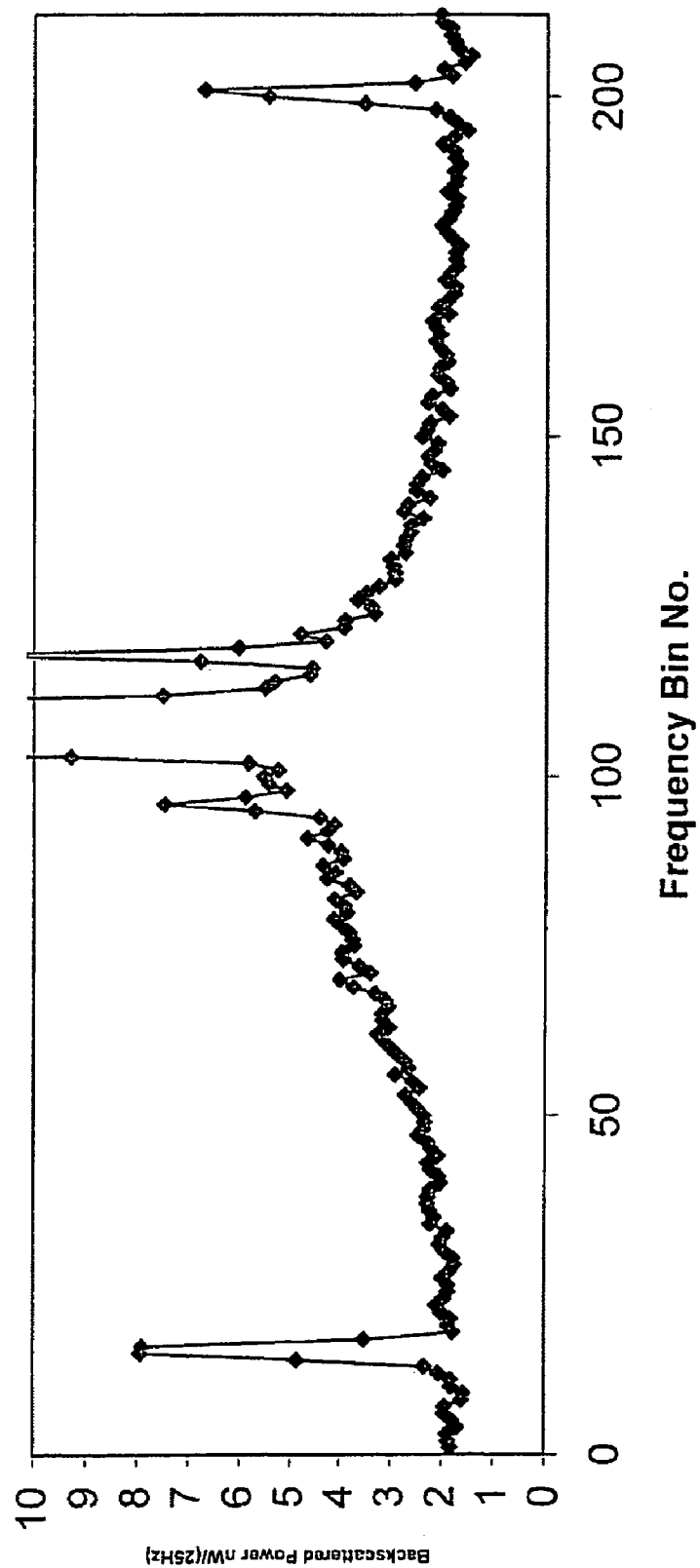
FIG. 19 is backscattered power spectrum for a stirred sample of 10% wt/wt carboxylated polystyrene beads, 40 nm diameter, according to one embodiment of the invention.

FIG. 19 shows a backscattered power spectrum for a stirred sample of 10% wt/wt carboxylated polystyrene beads, 40 nm diameter. The peaks at bins near 10, 95, 110 and 200 are electronic artifacts. Doppler shifted power clearly evident above bin 50 and below bin 150, may demonstrate the ability of the system according to embodiments of the invention to detect this type of nanoparticle.

Figure 20:
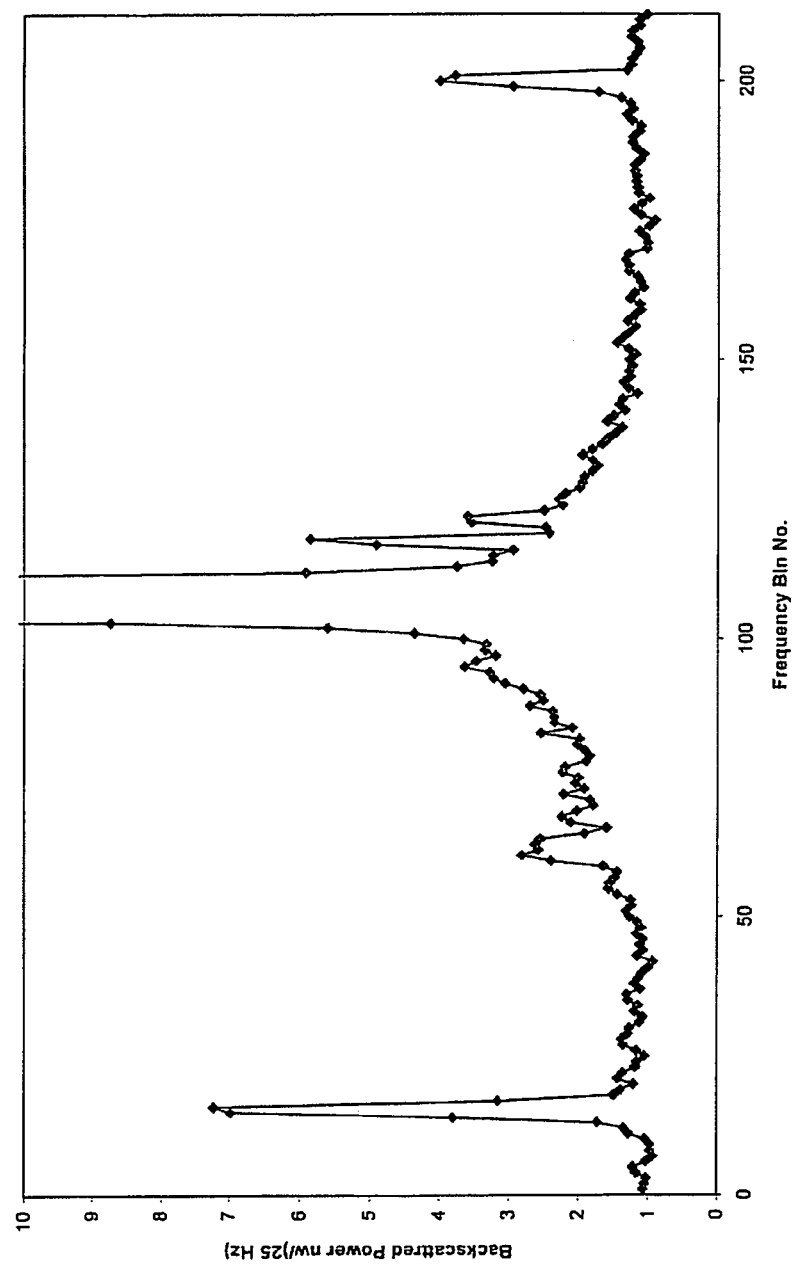
FIG. 20 is Backscattered power spectrum for a stirred sample of 5% wt/wt STARBURST™ PAMAM Ethylenediamine core, tris surface 4.5 nm diameter dendrimer, according to one embodiment of the invention.

FIG. 20 shows a backscattered power spectrum for a stirred sample of 5% wt/wt STARBURST™ PAMAM Ethylenediamine core, tris surface 4.5 nm diameter dendrimer. The peaks at bins near 10, and 200 are electronic artifacts. Doppler shifted power clearly evident above bin 50 and below bin 150 may demonstrate the ability of the system according to embodiments of the invention to detect this type of nanoparticle.

Figure 21:
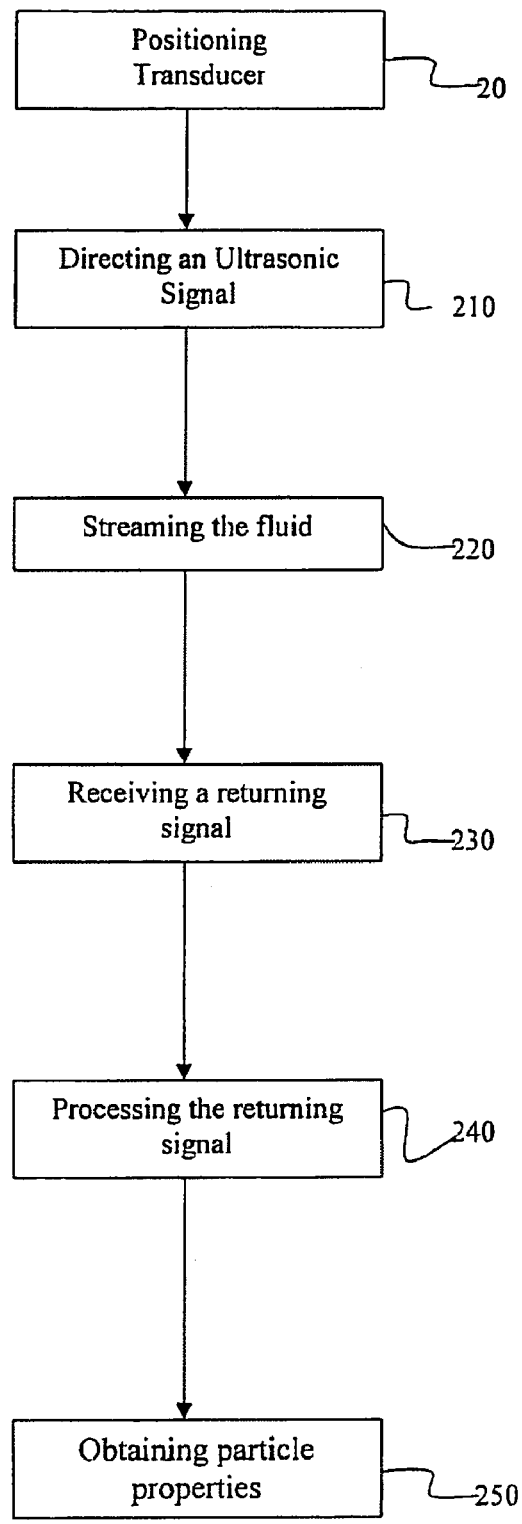
FIG. 21 is schematic illustration of a method for ultrasonic measuring of particle properties according to one embodiment of the invention.

Reference is now made to FIG. 21, which schematically illustrates a method for ultrasonic measuring of particle properties according to an embodiment of the invention.

In block 200 a transducer may be positioned in acoustic contact with suspension or sample, e.g., sample 112 of FIG. 1. This may not require physical contact with the suspension. For example, the transducer may be inserted into a test chamber which may include the sample, e.g., test chamber 113 of FIG. 1, from the top, bottom or side through for example a hole or other opening. It may be situated outside a test chamber with adequately acoustically transparent walls. The transducer, for example, transducer 105 of FIG. 1 may have a resonant flat piezoelectric ceramic crystal and a concave elastomeric focusing lens. Other suitable transducers may be used, for example, transducers with shaped piezoelectric elements to provide the focusing function. The transducer may have different diameters and focal lengths, such as for example, 4 mm and focal lengths of 1.6 mm, and an outer diameter of 6 mm and focal lengths of 7 mm. For example, the focal length of the transducer may be on the order of 1.6 mm and the focal volume or focal zone in the vicinity of the focus may be a fraction of a cubic millimeter. Any other suitable transducers with any diameters and focal lengths may be used. Any suitable numbers of transducer may be used, for example, for generating more than one signal, or to transmit a signal with one transducer and to receive the backscattered signal with another transducer.

In block 210 an ultrasonic signal may be directed from a transducer towards the particles in the suspension. The ultrasonic signal may be focused to a focal zone in the suspension. The signal may for example include a series of tone bursts, for example, of equal length at the selected center frequency. For example, frequencies between 7 and 20 MHz and tone burst lengths from 20 to 200 cycles may be used. Other frequency ranges and tone burst lengths may be used In one embodiment the string of tone bursts of a single frequency may be long, for example, tens of milliseconds and the tone bursts may be tens of cycles long, thus each burst may be several microseconds long, these may be repeated every few microseconds. For example, a signal of 40 millisecond long consisting of a string of 20 cycle-long (1.3 microseconds) tone bursts of a single frequency, of 15 Mhz may be repeated every 7 microseconds. The tone burst may include 20-100 cycles. In the period in between bursts, the interrogating signal may be turned off.

In block 220 the fluid of suspension may be subjected to acoustic streaming or otherwise placed in motion, which may give rise to velocities of particles in suspension which may also stir the fluid. The ultrasonic interrogating signal may be used to induce streaming of the particles near the focal zone. The streaming may be generated by the radiation pressure of the acoustic energy of the transmitted signal on the fluid of the suspension. It may be enhanced by the high levels of acoustic energy in the focal volume due to the large acoustic field there which may be produced by for example focusing and the use of narrow band interrogating signals. In some embodiments of the invention streaming may allow Doppler effect mediated measurements of particle velocities without any other source of velocity.

According to one embodiment of the invention when streaming is used as a source of velocity or movement the resulting spectra may show peaks on the order of a few bins wide, for example, about 10, representing 250 Hz range of frequencies or about a 1 cm/sec range of velocities. These may indicate particle motions at the velocity corresponding to the Doppler shift associated with the frequency difference between these peaks and the main peak which represents the interrogating signal.

In block 230 a return signal backscattered from the particles in the suspension may be received. The returning signal may be received during the intervals between the tone bursts of the directed or transmitted ultrasonic signal and may include frequencies that may differ from that of the transmitted ultrasonic signal. In the period in between bursts, when the interrogating signal may be turned off backscattered signals may return from the focal zone, e.g., the returning signal may be received during the intervals between the tone bursts of the transmitted interrogating ultrasonic signal. The returned, backscattered signal may fall between the tone bursts, where the signal is turned off. The received signal may include of the original signal with the backscattered signals, of power received from particles, falling between the interrogating signals.

In block 240 the return signal may be processed to obtain properties of the particles, such as velocity, concentration and size of the particles. The analyzing and processing of the received signal may include a calculation of a high resolution power spectrum of the signal containing the incident and reflected signals.

The processing of the return signal may include obtaining the power spectrum of the returning signal by applying a FFT and/or by applying a narrow band filter. The signal processing requirements for the formation of the FFT may be, for example, sampling a 16 MHz signal, which may require a Nyquist sampling rate of at least 32 million samples/sec. The FFT may have adequate frequency resolution to produce spectra with adequate detail to capture the spectral shape defined by the fluid flow in the sample.

The processing of the returning signal may include separating a reflected signal from a back wall surrounding the suspension 1 in the time domain. One embodiment of the present invention may self-calibrate by measuring the reflected signal from the back wall of the chamber, a target with constant properties.

The BWR may fall midway in time between the tone bursts of the signal. The BWR may be used as a self-test or may be used to calibrate the system. Such testing or calibration may be performed in for example the time domain or in the frequency domain.

In block 250 particle properties may be obtained and/or output, for example on a monitor of a PC or workstation. The reflected processed spectra of the reflected signal may provide information about the nature of the particles. For example, multiple spectra peaks may imply the existence of more than one type of particle and the velocities with which these particles move may provide information about them and the viscosity of the suspensions.

Backscatter from the suspension may occur in a band of Doppler-shifted frequencies, due in part to the distribution of particle velocities (or more precisely of the components of these velocities in the direction of the line between the scatterer and the transducer). The shape of the reflectivity spectrum (e.g. backscattered power vs. frequency) may contain additional information about the particles. For example, the maximum velocity that can be induced by a given level of stirring or acoustical streaming depends on the viscosity of a sample likewise, under the influence of streaming alone, particles of different size may attain different velocities depending on possible particle interactions with the high acoustic fields or differing drag coefficients. In such cases, the reflection spectrum may include multiple peaks corresponding to the particle sizes.

The methods of this invention are useful in determining molecular size of a particular material. In one embodiment, the methods are useful in determining size of the material which is non-uniform in terms of its density, compressibility, etc. In some embodiments, the methods are useful in determining parameters for materials of different sizes within a single suspension. In some embodiments, the particles/molecules have a diameter ranging from 1-10,000 nanometers. In some embodiments, the material being evaluated by the methods of this invention is a biologic material, such as a cell, or cellular matter, tissue homogenates, and the like. In some embodiments, reference to the term "particle" is to be understood to include such material, which is measurable by the methods of the invention, such as cells, homogenates, etc., as described.

In one embodiment, this invention provides a method for measuring properties of particles in a suspension, the method comprising directing an ultrasonic signal having single frequency tone bursts of at least 10 cycles toward the particles, receiving a return signal reflected or backscattered from the particles and generating a power spectrum by processing the return signal to obtain properties of the particles. In one embodiment, the ultrasonic signal has single frequency tone bursts of at least 10, or in another embodiment, at least 15, or in another embodiment, at least 20, or in another embodiment, at least 25, or in another embodiment, at least 40, or in another embodiment, at least 60, or in another embodiment, at least 75, or in another embodiment, at least 100, or in another embodiment, at least 200, or in another embodiment, at least 500, or in another embodiment, from 10-250, or in another embodiment, from 15-100 cycles.

In one embodiment, the term "reflected" or "reflect" in connection with the methods and/or materials of this invention is to be understood to include backscatter, sidescatter, frontscatter, or combinations thereof, of the energy serving as the return signal.

In one embodiment, "subtraction" refers to a mathematical manipulation whereby values obtained are removed to produce the difference in the values. In one embodiment, the term "subtraction" refers to any means of discounting particular values obtained, without necessarily involving physical removal of the values from an equation, for example, a spectra that is visibly irrelevant is discounted or thereby subtracted.

In one embodiment, the term "high resolution" in connection with the methods of this invention is to be understood to refer to high precision, and vice versa, e.g., a power spectrum with very narrow frequency bin widths.

Embodiments of the invention include the use of ultrasonic backscatter to characterize a desired parameter, for example, concentration, particle size, viscosity of suspension, etc., for example, in samples containing islets, cells, nanoparticles and the like. Some embodiments may use of an interrogating signal to produce velocities and Doppler shifts by Eckart streaming, and generate high resolution, very narrow bin width backscatter power spectra which may allow determination of detailed spectral shape of backscatter which makes possible measurement of, for example, concentration by adding up the power in the spectra away from the main peak, particle size by measuring the velocities generated by Eckart streaming with other velocity generating means not working. Other measurement may be done.

Embodiments of the invention may use BWR to calibrate the system, and also may combine focused transducer with narrowband signals to produce high power in small volumes and narrow frequency ranges. This may allow generation of large Doppler shifted signals within a few hundred hertz of the main peak due to the interrogating signals, regardless of the source of velocity. This combination may also create streaming and velocity.

It is to be understood that any material which may be used according to the methods of this invention is to be considered within the scope of this invention.

It will be appreciated by persons skilled in the art that the present invention is not limited by what has been particularly shown and described hereinabove. Rather the scope of the invention is defined by the claims that follow:

The invention claimed is:

1. A method for measuring properties of particles in a suspension, the method comprising:
    directing an ultrasonic signal having a number of identical single frequency tone bursts of at least 10 cycles toward the particles;
    receiving a return signal backscattered from the particles; and
    generating a high resolution power spectrum by processing the return signal to obtain properties of the particles;
    wherein processing the return signal comprises estimating the energy contained in off-peak bins of the power spectrum, wherein off-peak bins represent frequencies altered from those of the tone bursts by Doppler frequency shifts due to velocity of the particles relative to a transducer and wherein estimating the energy comprises summing the power of plurality of off-peak bins.

2. The method of claim 1, wherein the ultrasonic signal induces motion of the particles relative to the transducer by acoustic streaming of the fluid containing the particles in and near a focal zone, which also comprises a region wherein the majority of the particle backscatter is generated.

3. The method of claim 1, wherein the particles are set into motion by the action of a stirrer, or wherein the particles are in motion due to bulk fluid flow.

4. The method of claim 1, wherein a single transducer is used both to direct the signal to the particles and to receive the backscattered return signal.

5. The method of claim 1, wherein directing the ultrasonic signal further comprises introduction of gaps between the single frequency tone bursts, and wherein the return signal is received during the gaps between the single frequency tone bursts.

6. The method of claim 1, wherein the single frequency is at a range of between 7 MHz and 30 MHz.

7. The method of claim 1, wherein the properties measured comprise velocity, size of the particles, concentration, viscosity of the suspension or a combination thereof.

8. The method of claim 1, wherein processing of the return signal comprises applying a several million point Fast Fourier Transform algorithm to the return signal to obtain a high resolution power spectrum, or applying a series of narrow band filters to the return signal to obtain a power spectrum.

9. The method of claim 1, wherein processing the return signal comprises displaying the high resolution power spectrum of the return signal in a frequency domain of narrow bin size, and wherein the bin size or frequency resolution is less than 200 Hz.

10. The method of claim 1, further comprising the step of obtaining background values of reflected or backscattered energy by directing an ultrasonic signal toward a fluid without said particles and subtracting said background values obtained from values obtained with particles present, in the frequency domain.

11. The method of claim 1, wherein processing the return signal comprises displaying the power spectrum of the return signal in a frequency domain of narrow bin size, and wherein the bin size is less than 25 Hz.

12. The method of claim 1, wherein processing the return signal comprises displaying the power spectrum of the return signal in a frequency domain of narrow bin size, and wherein the bin size is roughly 1 Hz, 25 Hz, 50 Hz, 100 Hz, 125 Hz, 150 Hz or 200 Hz.

13. The method of claim 1, wherein said particles are in motion.

14. The method of claim 13, wherein said motion is caused by bulk flow, stirring or a combination thereof.

15. The method of claim 13, wherein said motion is induced by said directed ultrasonic signal.

16. The method of claim 15, wherein said induced motion is associated with acoustic streaming induced in the fluid.

17. The method of claim 1, further comprising a step of self test or calibration.

18. The method of claim 1, wherein said ultrasonic signal is focused.

19. The method of claim 18, wherein said focusing causes the bulk of said backscattered signal to be generated in a small focus volume.

20. The method of claim 1, wherein said power spectrum has a high resolution.

21. The method of claim 1, further comprising the steps of, obtaining background values of reflected or backscattered energy by directing an ultrasonic signal toward a fluid comprising particles to which no stirring or other means of introducing velocity are applied so that said particles are not set into motion and said particles remain suspended or fall to the boftom of the measurement vessel, and subtracting said background values obtained from values obtained when stirring or other means of introducing velocity is applied to said fluid, such that particles are in motion throughout the measurement vessel.

22. The method of claim 1, wherein the ultrasonic signal generates high intensity without generating streaming, in a focal zone which comprises a region wherein the majority of the particle is generated.

23. A method for measuring properties of particles in a suspension, the method comprising:
    directing an ultrasonic signal having several identical single frequency tone bursts of at least 10 cycles toward the particles;
    receiving a retum signal backscattered from the particles; and
    generating a high resolution power spectrum by processing the return signal to obtain properties of the particles;
    wherein said particles are in motion and wherein said motion results in said backscattered signal having a frequency that is Doppler-shifted with respect to said directed single frequency.

24. A method for measuring properties of particles in a suspension, the method comprising:
- directing an ultrasonic signal having several identical single frequency tone bursts of at least 10 cycles toward the particles;
- receiving a return signal backscattered from the particles; and
- generating a high resolution power spectrum by processing the return signal to obtain properties of the particles;

wherein said method further comprises a step of self test or calibration and wherein said self test or calibration is performed using back wall reflection (BWR).

* * * * *

UNITED STATES PATENT AND TRADEMARK OFFICE
CERTIFICATE OF CORRECTION

| | | |
|---|---|---|
| PATENT NO. | : 7,543,480 B2 | Page 1 of 1 |
| APPLICATION NO. | : 11/272032 | |
| DATED | : June 9, 2009 | |
| INVENTOR(S) | : Africk et al. | |

It is certified that error appears in the above-identified patent and that said Letters Patent is hereby corrected as shown below:

Col. 1 lines 13-14, please replace with the following,

This invention was made with government support under grant number R43 DK063727 awarded by the National Institutes of Health. The government has certain rights in this invention.

Signed and Sealed this
Twenty-third Day of August, 2011

David J. Kappos
*Director of the United States Patent and Trademark Office*